(12) United States Patent
Malkowski

(10) Patent No.: US 10,806,441 B2
(45) Date of Patent: Oct. 20, 2020

(54) ENDOSCOPIC STITCHING DEVICE

(71) Applicant: Covidien LP, Mansfield, MA (US)

(72) Inventor: Jaroslaw T. Malkowski, Trumbull, CT (US)

(73) Assignee: Covidien LP, Mansfield, MA (US)

( * ) Notice: Subject to any disclaimer, the term of this patent is extended or adjusted under 35 U.S.C. 154(b) by 149 days.

(21) Appl. No.: 16/120,487

(22) Filed: Sep. 4, 2018

(65) Prior Publication Data

US 2019/0133569 A1    May 9, 2019

Related U.S. Application Data

(60) Provisional application No. 62/581,061, filed on Nov. 3, 2017.

(51) Int. Cl.
*A61B 17/04* (2006.01)
*A61B 17/06* (2006.01)
(Continued)

(52) U.S. Cl.
CPC ...... *A61B 17/0469* (2013.01); *A61B 17/0482* (2013.01); *A61B 17/0625* (2013.01); *A61B 17/06166* (2013.01); *A61B 17/2909* (2013.01); *A61B 17/06066* (2013.01); *A61B 2017/0046* (2013.01); *A61B 2017/00367* (2013.01); (Continued)

(58) Field of Classification Search
CPC ............ A61B 17/0482; A61B 17/0469; A61B 17/06166; A61B 17/0625; A61B 17/2909; A61B 17/06066; A61B 17/1285; A61B 2017/2913; A61B 2017/2919; A61B 2017/2922; A61B 2017/2923
See application file for complete search history.

(56) References Cited

U.S. PATENT DOCUMENTS 1,037,864 A   9/1912  Carlson et al.
1,131,163 A   3/1915  Saunders et al.
(Continued)

FOREIGN PATENT DOCUMENTS

WO    2008045333 A2    4/2008

OTHER PUBLICATIONS

International Search Report issued in corresponding Application No. PCT/US2018/057425, dated Feb. 11, 2019 (13 pages).

*Primary Examiner* — Tuan V Nguyen
(74) *Attorney, Agent, or Firm* — Carter, DeLuca & Farrell LLP

(57) ABSTRACT

An endoscopic stitching device includes a handle assembly and an elongate shaft assembly. The handle assembly includes a main rod, a drive conversion assembly, and an unloading lock. The drive conversion assembly includes a cam wheel, a pivot block, links interconnecting the pivot block with the cam wheel, a pawl configured to engage the pivot block to rotate the pivot block, and a pusher. The unloading lock is transitionable between an engaged position in which the unloading lock engages the pusher to inhibit distal movement of the pusher, and a disengaged position in which the pusher is movable to a distal-most position. The elongate shaft assembly includes first and second blade drive members coupled with the cam wheel and a tool assembly including first and second jaws coupled with the main rod, and first and second blades coupled with the first and second blade drive members, respectively.

26 Claims, 19 Drawing Sheets

(51) Int. Cl.
  *A61B 17/29*   (2006.01)
  *A61B 17/062*   (2006.01)
  *A61B 17/00*   (2006.01)
  *A61B 90/00*   (2016.01)

(52) U.S. Cl.
  CPC .............. *A61B 2017/06176* (2013.01); *A61B 2017/2901* (2013.01); *A61B 2017/2913* (2013.01); *A61B 2017/2926* (2013.01); *A61B 2017/2936* (2013.01); *A61B 2090/034* (2016.02)

(56) References Cited

U.S. PATENT DOCUMENTS

| | | |
|---|---|---|
| 1,293,565 A | 2/1919 | Smit |
| 1,449,087 A | 3/1923 | Bugbee |
| 1,876,792 A | 9/1932 | Thompson |
| 2,213,830 A | 9/1940 | Anastasi |
| 2,880,728 A | 4/1959 | Rights |
| 3,090,386 A | 5/1963 | Curtis |
| 3,349,772 A | 10/1967 | Rygg |
| 3,470,875 A | 10/1969 | Johnson |
| 3,807,407 A | 4/1974 | Schweizer |
| 3,842,840 A | 10/1974 | Schweizer |
| 3,901,244 A | 8/1975 | Schweizer |
| 3,946,740 A | 3/1976 | Bassett |
| 4,021,896 A | 5/1977 | Stierlein |
| 4,109,658 A | 8/1978 | Hughes |
| 4,161,951 A | 7/1979 | Scanlan, Jr. |
| 4,164,225 A | 8/1979 | Johnson et al. |
| 4,236,470 A | 12/1980 | Stenson |
| 4,345,601 A | 8/1982 | Fukuda |
| 4,373,530 A | 2/1983 | Kilejian |
| 4,471,781 A | 9/1984 | Di Giovanni et al. |
| 4,491,135 A | 1/1985 | Klein |
| 4,580,567 A | 4/1986 | Schweitzer et al. |
| 4,621,640 A | 11/1986 | Mulhollan et al. |
| 4,635,638 A | 1/1987 | Weintraub et al. |
| 4,890,615 A | 1/1990 | Caspari et al. |
| 4,923,461 A | 5/1990 | Caspari et al. |
| 4,935,027 A | 6/1990 | Yoon |
| 4,957,498 A | 9/1990 | Caspari et al. |
| 5,059,201 A | 10/1991 | Asnis |
| 5,100,421 A | 3/1992 | Christoudias |
| 5,171,257 A | 12/1992 | Ferzli |
| 5,181,919 A | 1/1993 | Bergman et al. |
| 5,207,693 A | 5/1993 | Phillips |
| 5,217,471 A | 6/1993 | Burkhart |
| 5,242,458 A | 9/1993 | Bendel et al. |
| 5,254,126 A | 10/1993 | Filipi et al. |
| 5,261,917 A | 11/1993 | Hasson et al. |
| 5,281,220 A | 1/1994 | Blake, III |
| 5,336,230 A | 8/1994 | Leichtling et al. |
| 5,454,823 A | 10/1995 | Richardson et al. |
| 5,674,229 A | 10/1997 | Tovey et al. |
| 5,814,054 A * | 9/1998 | Kortenbach ........ A61B 17/0469 606/139 |
| 5,908,428 A * | 6/1999 | Scirica ............... A61B 17/0469 206/339 |
| 5,980,538 A | 11/1999 | Fuchs et al. |
| 6,270,508 B1 | 8/2001 | Klieman et al. |
| 7,588,583 B2 | 9/2009 | Hamilton et al. |
| 8,177,794 B2 | 5/2012 | Cabrera et al. |
| 8,226,667 B2 | 7/2012 | Viola et al. |
| 8,246,637 B2 | 8/2012 | Viola et al. |
| 8,292,905 B2 | 10/2012 | Taylor et al. |
| 8,292,906 B2 | 10/2012 | Taylor et al. |
| 8,337,515 B2 | 12/2012 | Viola et al. |
| 8,372,090 B2 | 2/2013 | Wingardner et al. |
| 8,454,631 B2 | 6/2013 | Viola et al. |
| 8,460,275 B2 | 6/2013 | Taylor et al. |
| 8,490,713 B2 | 7/2013 | Furnish et al. |
| 8,496,674 B2 | 7/2013 | Cabrera et al. |
| 8,506,581 B2 | 8/2013 | Wingardner, III et al. |
| 8,628,545 B2 | 1/2014 | Cabrera et al. |
| 8,636,752 B2 | 1/2014 | Cabrera et al. |
| 8,747,424 B2 | 6/2014 | Taylor et al. |
| D708,746 S | 7/2014 | Cabrera et al. |
| 8,864,776 B2 | 10/2014 | Bogart et al. |
| 8,968,340 B2 | 3/2015 | Chowaniec et al. |
| 8,968,342 B2 | 3/2015 | Wingardner, III et al. |
| 9,113,860 B2 | 8/2015 | Viola et al. |
| 9,271,723 B2 | 3/2016 | Taylor et al. |
| 9,615,824 B2 | 4/2017 | Furnish et al. |
| 9,675,340 B2 | 6/2017 | Sniffin et al. |
| 2004/0260314 A1 | 12/2004 | Lizardi |
| 2005/0149066 A1 | 7/2005 | Stafford |
| 2006/0020274 A1 | 1/2006 | Ewers |
| 2009/0221868 A1 | 9/2009 | Evans |
| 2009/0299406 A1 | 12/2009 | Swain |
| 2009/0312773 A1 | 12/2009 | Cabrera et al. |
| 2010/0228270 A1 | 9/2010 | Bogart et al. |
| 2011/0040308 A1 | 2/2011 | Cabrera et al. |
| 2012/0215234 A1* | 8/2012 | Chowaniec ........ A61B 17/0469 606/144 |
| 2013/0023725 A1 | 1/2013 | Nose |
| 2017/0150962 A1 | 6/2017 | Cabrera et al. |

* cited by examiner

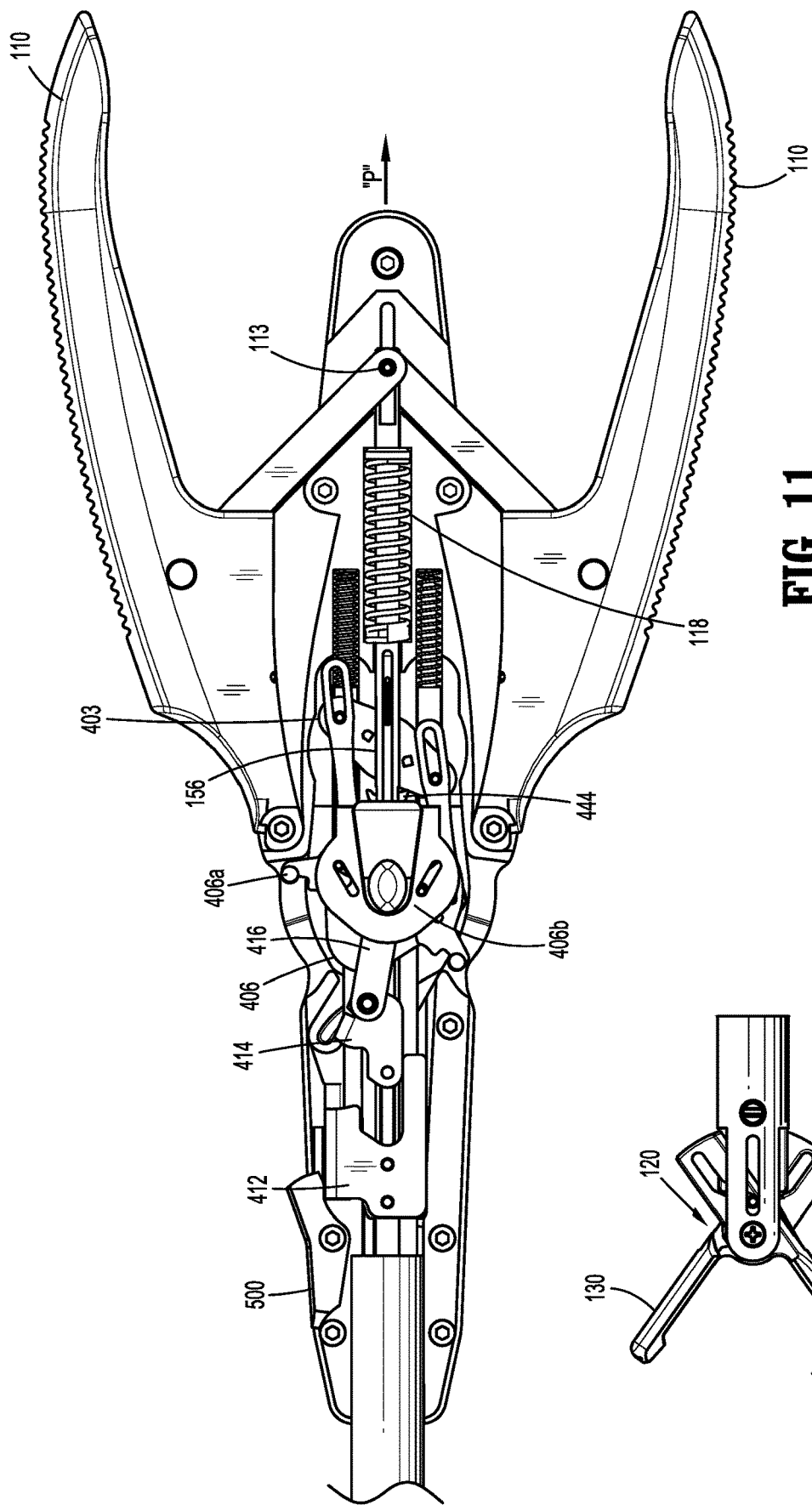
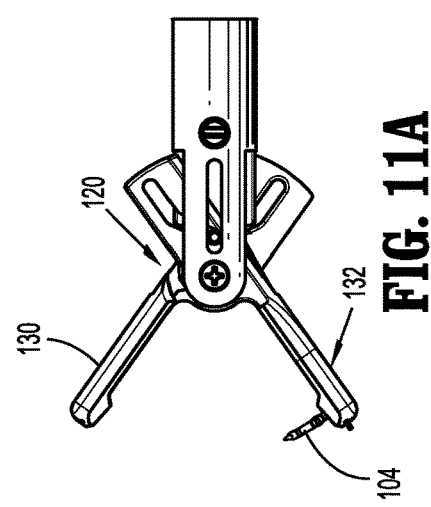
FIG. 11
FIG. 11A

ENDOSCOPIC STITCHING DEVICE

CROSS-REFERENCE TO RELATED APPLICATION

This application claims the benefit of and priority to U.S. Provisional Patent Application No. 62/581,061 filed Nov. 3, 2017, the entire disclosure of which is incorporated by reference herein.

BACKGROUND

Technical Field

The present disclosure relates to devices for suturing or stitching and, more particularly, to devices for endoscopic suturing and/or stitching through an access tube or the like.

Background

One of the advances in recent years to reduce the invasiveness of surgical procedures is endoscopic surgery. Generally, endoscopic surgery involves incising through body walls. Typically, trocars are utilized for creating the incisions through which the endoscopic surgery is performed. Trocar tubes or cannula devices are extended into and left in place in the abdominal wall to provide access for endoscopic surgical tools. A camera or endoscope is inserted through a relatively large diameter trocar tube which is generally located at the naval incision, and permits the visual inspection and magnification of the body cavity. The surgeon can then perform diagnostic and therapeutic procedures at the surgical site with the aid of specialized instrumentation, such as, forceps, cutters, applicators, and the like which are designed to fit through additional cannulas.

In many surgical procedures, including those involved in endoscopic surgery, it is often necessary to suture bodily organs or tissue. Suturing may be challenging during endoscopic surgery because of the small openings through which the suturing of bodily organs or tissues must be accomplished. Accordingly, a need exists for simple and effective devices for endoscopic suturing or stitching.

SUMMARY

The present disclosure describes a device for suturing and stitching that demonstrates a practical approach to meeting the performance requirements and overcoming usability challenges associated with endoscopic suturing or stitching. In accordance with an embodiment of the present disclosure, there is provided an endoscopic stitching device including a handle assembly and an elongate shaft assembly.

The handle assembly includes a main rod configured for axial displacement, a drive conversion assembly, and an unloading lock. The drive conversion assembly includes a cam wheel, a pivot block, first and second links interconnecting the pivot block with the cam wheel, a pawl operatively coupled to the main rod, and a pusher secured with the main rod and operatively coupled with the cam wheel. In particular, the pawl is configured to engage the pivot block to rotate the pivot block which, in turn, causes reciprocating displacement of the first and second links. The unloading lock is transitionable between an engaged position in which the unloading lock engages the pusher to inhibit distal movement of the pusher, and a disengaged position in which the pusher is disengaged from the unloading lock such that the pusher is movable to a distal-most position. The elongate shaft assembly includes a tool assembly and first and second blade drive members operatively coupled with the cam wheel. The tool assembly includes first and second jaws operatively coupled with the main rod of the handle assembly and first and second blades slidably disposed in the respective first and second jaws. The first and second blades are operatively coupled with the first and second blade drive members, respectively. Axial displacement of the main rod transitions the first and second jaws between open and closed positions and causes reciprocating axial displacement of the first and second blades.

In an embodiment, the handle assembly may include a housing pivotably supporting the unloading lock.

In another embodiment, the unloading lock may include a first portion and a second portion configured to engage the pusher. The first and second portions may define a curvature such that that when the unloading lock is in the disengaged position, the first portion is flush with the housing and the second portion protrudes from the housing.

In yet another embodiment, when the unloading lock is in the engaged position the second portion may be flush with the housing and the first portion may protrude from the housing.

In still another embodiment, the pusher may define a cutout, and the second portion of the unloading lock may include an engaging portion configured to engage the cutout of the pusher.

In a further embodiment, the engaging portion of the unloading lock may be proximal of the cutout of the pusher when the pusher is in the distal-most position.

In still another embodiment, the unloading lock may be disposed transverse to a longitudinal axis of the handle assembly.

In yet another embodiment, the unloading lock may be aligned with a longitudinal axis defined by the handle assembly when the unloading lock is in the disengaged position.

In still yet another embodiment, the unloading lock may be offset from a longitudinal axis defined by the handle assembly when the unloading lock is in the engaged position.

In another embodiment, the pusher may include walls defining a slot therebetween.

In a further embodiment, the unloading lock may include a finger dimensioned to be received in the slot of the pusher to enable axial displacement of the pusher to the distal-most position.

In still yet another embodiment, the finger of the unloading lock may be configured to engage the walls to inhibit axial displacement of the pusher to the distal-most position.

In accordance with aspect of the present disclosure, there is provided a handle assembly for use with an endoscopic stitching device. The handle assembly includes a main rod configured for axial displacement, a drive conversion assembly, and an unloading lock. In particular, the drive conversion assembly includes a cam wheel, a pivot block, first and second links interconnecting the pivot block with the cam wheel, a pawl operatively coupled to the main rod, third and fourth links operatively coupled with the cam wheel, and a pusher operatively coupled to the main rod, the pusher engaging the third link to exert force on the cam wheel. The pawl is configured to engage the pivot block to rotate the pivot block which, in turn, causes reciprocating displacement of the first and second links. The unloading lock is transitionable between an engaged position in which the unloading lock engages the pusher to inhibit distal movement of the pusher, and a disengaged position in which the pusher is movable to a distal-most position.

In another embodiment, the unloading lock may include a first portion and a second portion. The second portion may include a finger having a width and a length larger than the width.

In still another embodiment, the first portion and the finger may be rotatable as a single construct.

In yet another embodiment, the length of the finger may be aligned with a longitudinal axis of the handle assembly when the unloading lock is in the engaged position.

In a further embodiment, the width of the finger may be aligned with a longitudinal axis of the handle assembly when the unloading lock is in the disengaged position.

In a further embodiment, the unloading lock may include a head portion including an arcuate profile, an engaging portion defining an arcuate recess, and a neck portion connecting the head portion and the engaging portion.

In yet another embodiment, the handle assembly may further include a housing, wherein when the unloading lock is in the disengaged position the head portion may protrude from the housing and the arcuate recess of the engaging portion may enable passage of the pusher therethrough, and when the unloading lock is in the engaged position, the head portion may extend transversely outward from the housing and the engaged portion may engage the pusher.

In still yet another embodiment, the housing may define a notch dimensioned to secure the neck portion of the unloading lock when the unloading lock is in the disengaged position.

DETAILED DESCRIPTION OF THE DRAWINGS

The foregoing objects, features and advantages of the disclosure will become more apparent from a reading of the following description in connection with the accompanying drawings, in which:

FIGS. 11 and 11A are partial top views of the stitching device of FIG. 1, illustrating jaws in an open position with a needle supported on a first jaw;

DETAILED DESCRIPTION

Figure 1:
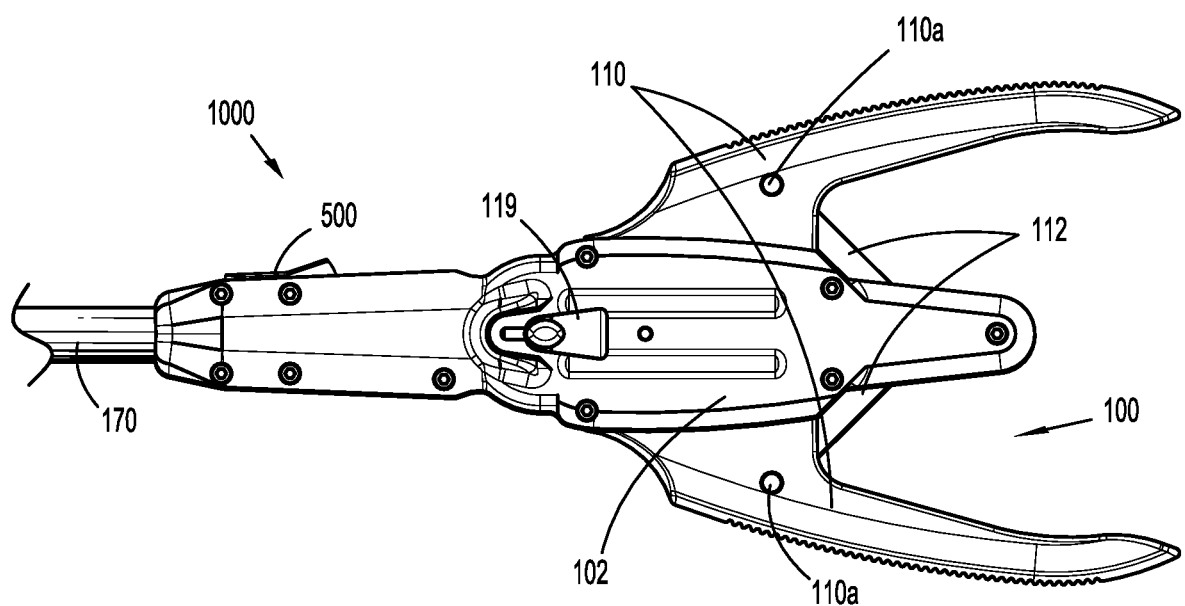
FIG. 1 is a partial top view of a stitching device in accordance with an embodiment of the present disclosure.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail.

Figure 2:
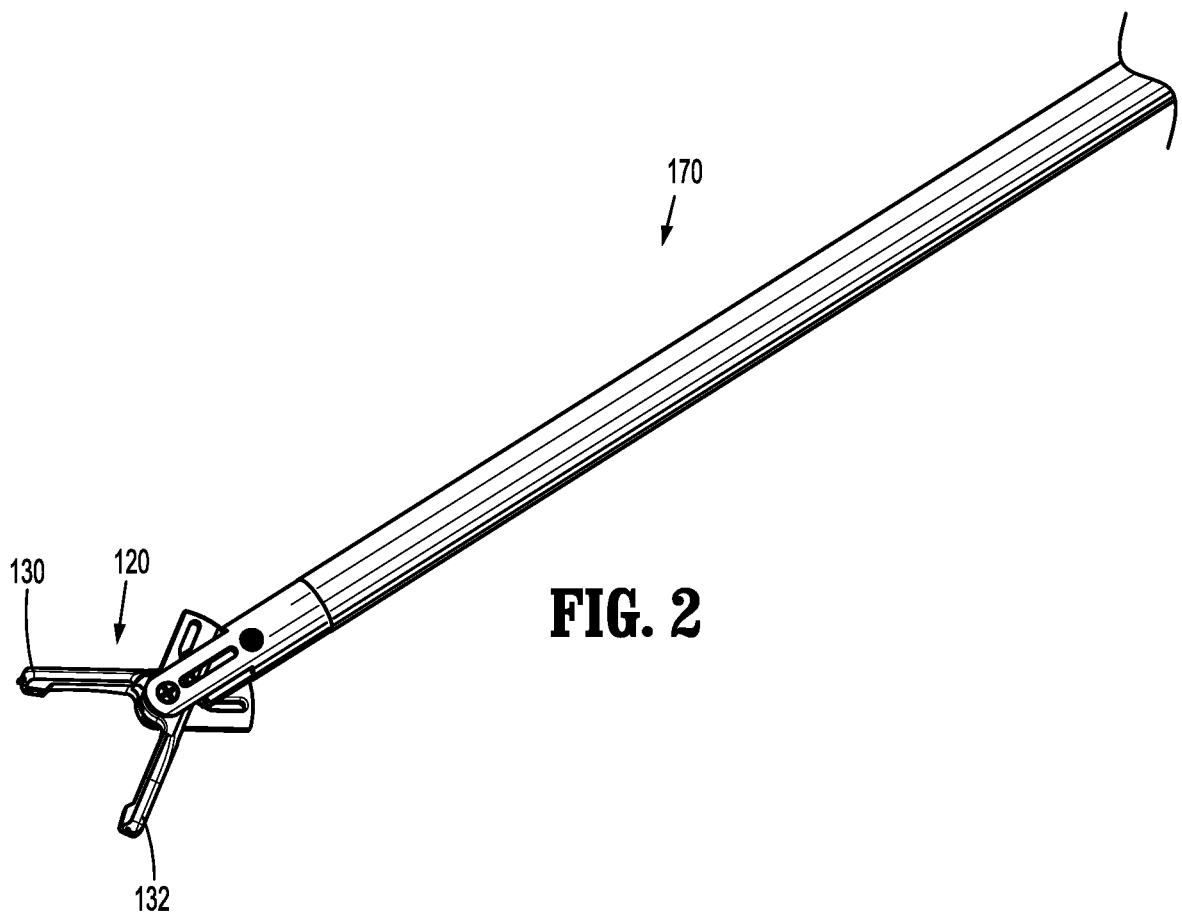
FIG. 2 is a perspective view of an elongate shaft assembly of the stitching device of FIG. 1.

With reference to FIGS. 1 and 2, an embodiment of an endoscopic stitching device of the present disclosure is generally shown as stitching device 1000. Stitching device 1000 is adapted to be particularly useful in endoscopic or laparoscopic procedures, wherein an endoscopic portion of stitching device 1000 such as, e.g., a tool assembly 120, is insertable into an operative site, via a cannula assembly or the like (not shown). Stitching device 1000 includes a handle assembly 100 and an elongate shaft assembly 170 extending distally from handle assembly 100. Handle assembly 100 includes an unloading lock 500 configured to selectively inhibit opening of jaws 130, 132 of tool assembly 120 before needle 104 (FIG. 5) is fully released from blades 150, 152 (FIG. 5) during unloading of needle 104 from jaws 130, 132, as will be described hereinbelow.

Figure 3:
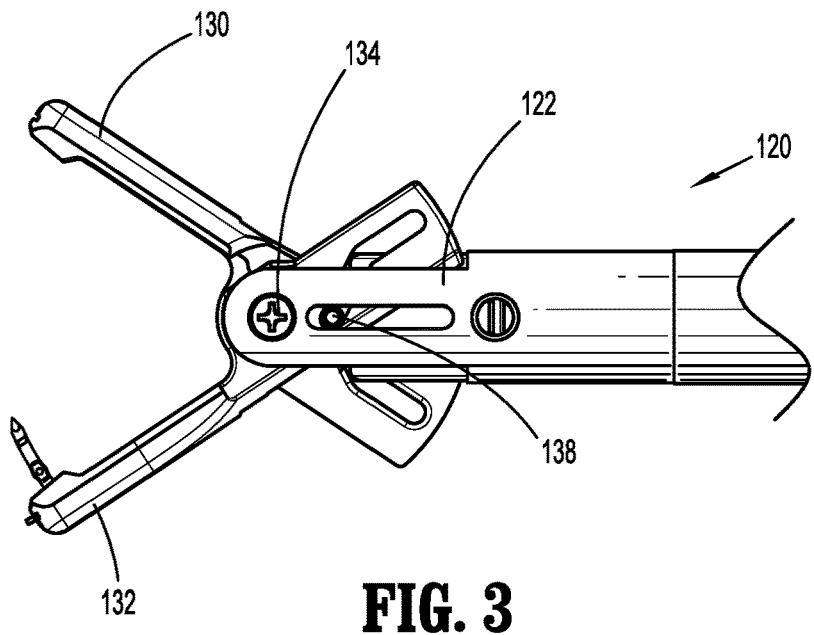
FIG. 3 is a top view of a tool assembly of the elongate shaft assembly of FIG. 2.
Figure 4:
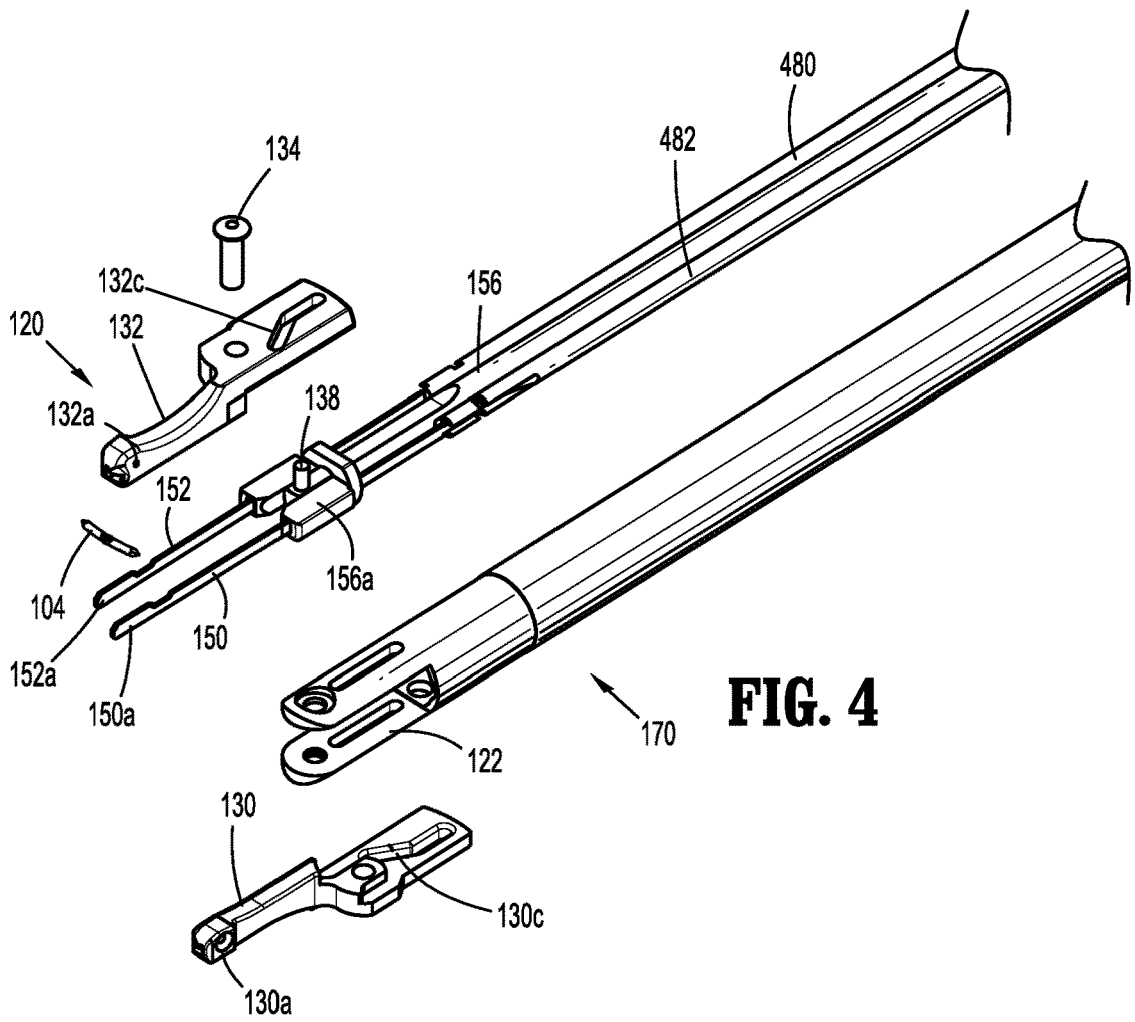
FIG. 4 is a perspective view, with parts separated, of the elongate shaft assembly of FIG. 2.
Figure 5:
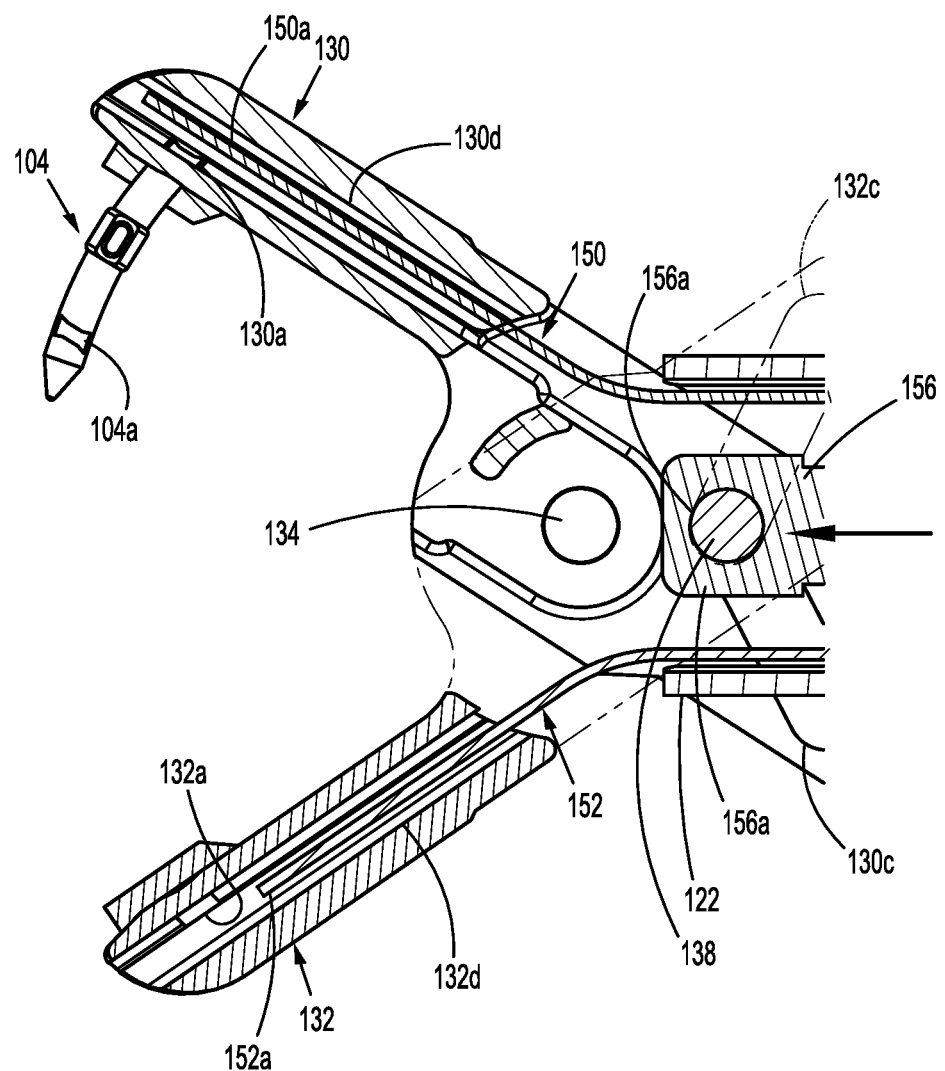
FIG. 5 is a partial, longitudinal cross-sectional view of the tool assembly of FIG. 3.

With reference to FIGS. 3-5, elongate shaft assembly 170 includes tool assembly 120. Tool assembly 120 includes a support member 122 and jaws 130, 132 pivotably mounted on support member 122 by means of a jaw pivot pin 134. To move jaws 130, 132 between an open position and a closed position, main rod 156 has a camming pin 138 mounted at a distal end 156a thereof. Camming pin 138 rides in angled camming slots 130c, 132c defined in respective jaws 130, 132 such that axial or longitudinal movement of main rod 156 causes jaws 130, 132 to be cammed between the open and closed positions.

With particular reference to FIG. 5, tool assembly 120 further includes a pair of needle engaging members or blades 150, 152 which are slidably supported within support member 122. Each blade 150, 152 includes a distal end 150a, 152a slidably extending into blade receiving channels 130d, 132d of respective jaws 130, 132. Channels 130d, 132d are dimensioned to at least partially intersect needle recesses 130a, 132a. Thus, by advancing blade 150 or 152 within respective channel 130d, 132d, distal end 150a, 152a of advancing blade 150, 152 engages or "locks in" a groove 104a formed in needle 104 when at least a portion of needle 104 is received within respective recesses 130a, 132a. A suture (not shown) may be secured to needle 104. The suture may include a plurality of barbs oriented to resist movement in a direction opposite to the direction of travel.

Figure 6:
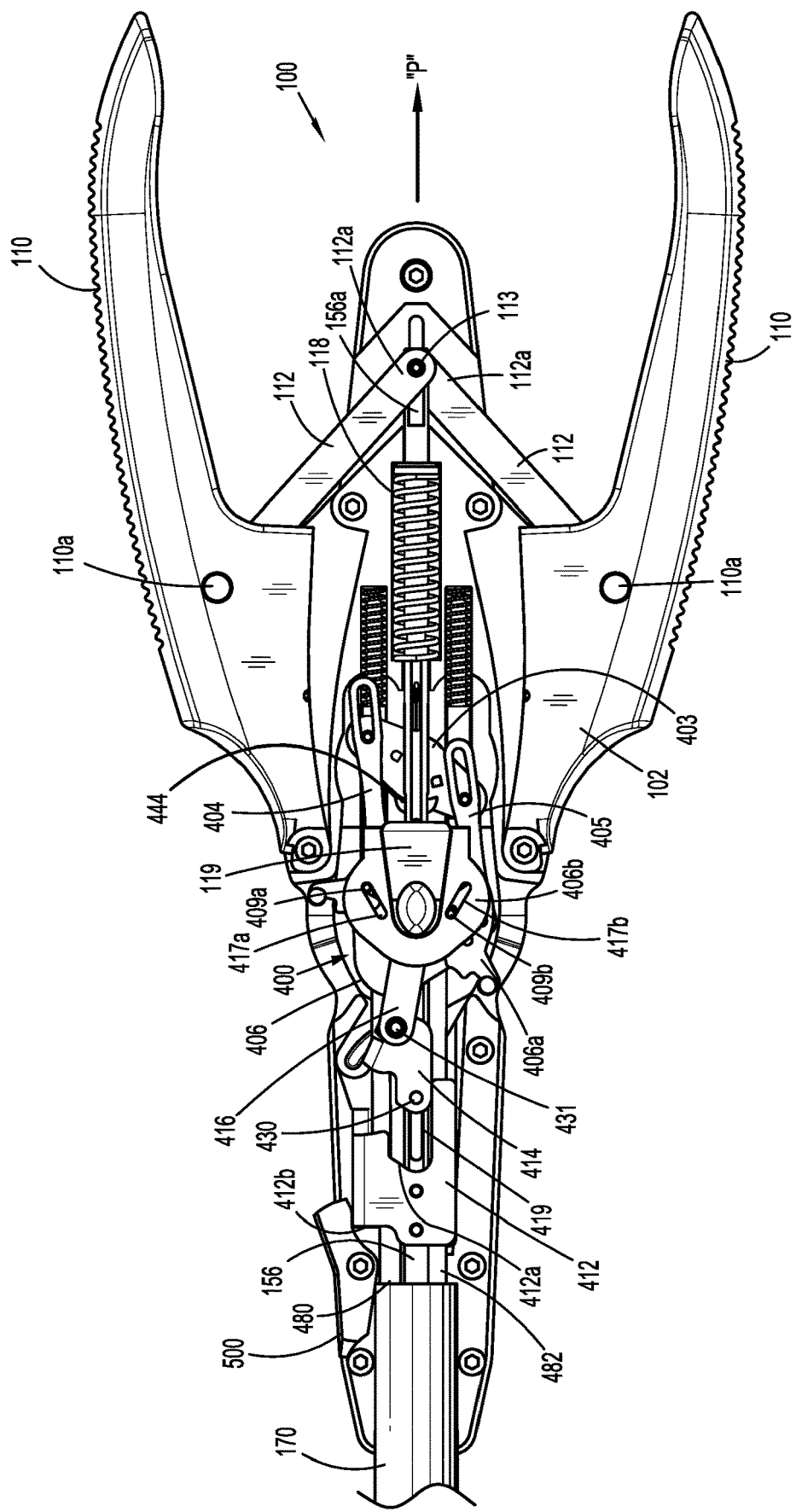
FIG. 6 is a top view of a handle assembly of FIG. 1 with a portion of a housing removed, illustrating a drive conversion assembly thereof.

With reference now to FIG. 6, handle assembly 100 includes a pair of handles 110 pivotably secured to housing 102. Handles 110 are operatively coupled by link members 112. Each link member 112 has a first end (not shown) pivotably connected to respective handles 110 at a pivot point 110a and a second end 112a pivotably connected to a proximal portion 156a of main rod 156 by a pin 113. Under such a configuration, when handles 110 are squeezed, link members 112 advance main rod 156 proximally in the direction of an arrow "p". Main rod 156 may be provided with, e.g., biasing members, in the form of a return spring 118, to bias main rod 156 toward the initial position. Main rod 156 is operatively coupled to jaws 130, 132 (FIG. 2) of tool assembly 120, such that axial displacement of main rod 156 transitions jaws 130, 132 between the open and closed positions.

With continued reference to FIG. 6, handle assembly 100 further includes first and second blade drive members 480, 482 extending through elongate shaft assembly 170. First and second blade drive members 480, 482 are coupled with respective blades 150, 152 (FIG. 5), such that reciprocating axial displacement of first and second blade drive members 480, 482 provides reciprocating axial displacement of blades 150, 152, enabling swapping of needle 104 between jaws 130, 132. Reference may be made to U.S. Pat. No. 8,628,545, entitled "Endoscopic Stitching Devices," the entire content of which is incorporated herein by reference, for a detailed description of the construction and operation of a handle assembly and a tool assembly.

With reference to FIGS. 6-9, handle assembly 100 includes drive conversion assembly 400 operatively coupled to main rod 156. Drive conversion assembly 400 is configured to convert axial displacement of main rod 156 into two reciprocating motions of blades 150, 152 (FIG. 5) of tool assembly 120. In this manner, axial displacement of main rod 156 effects both functions of opening and closing jaws 130, 132 and providing reciprocating axial displacement of blades 150, 152, thereby eliminating the need for a separate toggle mechanism to move blades 150, 152 (FIG. 5) in opposite directions.

With particular reference to FIG. 6, drive conversion assembly 400 includes a pusher 412 and links 414, 416. Pusher 412 is coupled to main rod 156 for concomitant movement therewith. Pusher 412 defines a cutout 412a having a shape complementary to a shape of a portion of link 414, and a second cutout 412b configured to engage unloading lock 500. In addition, a portion of main rod 156, in registration with cutout 412a of pusher 412, defines a slot 419. Link 414 includes a pin 430 slidably engaging slot 419 of main rod 156. Link 416 is pivotably coupled with link 414 by a pin 431. With brief reference to FIG. 8, link 416 includes a proximal portion 416a defining a bore 416b dimensioned to rotatably receive a protrusion 417 of a base portion 406a of a cam wheel 406.

Figure 7:
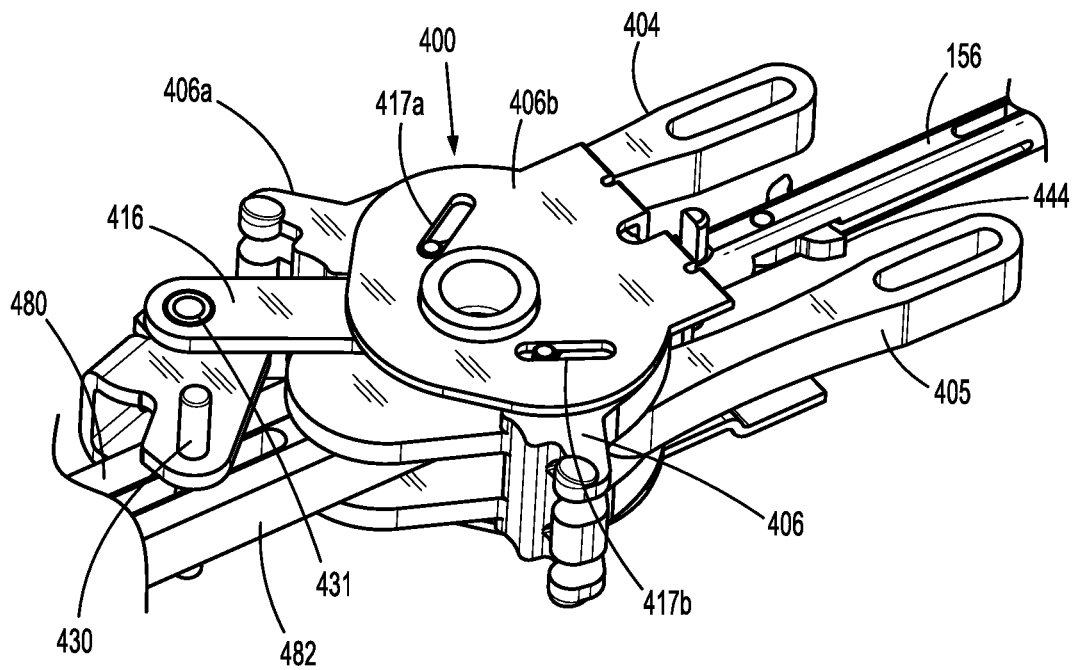
FIG. 7 is a perspective view of the drive conversion assembly of FIG. 6 with a pivot block removed.
Figure 8:
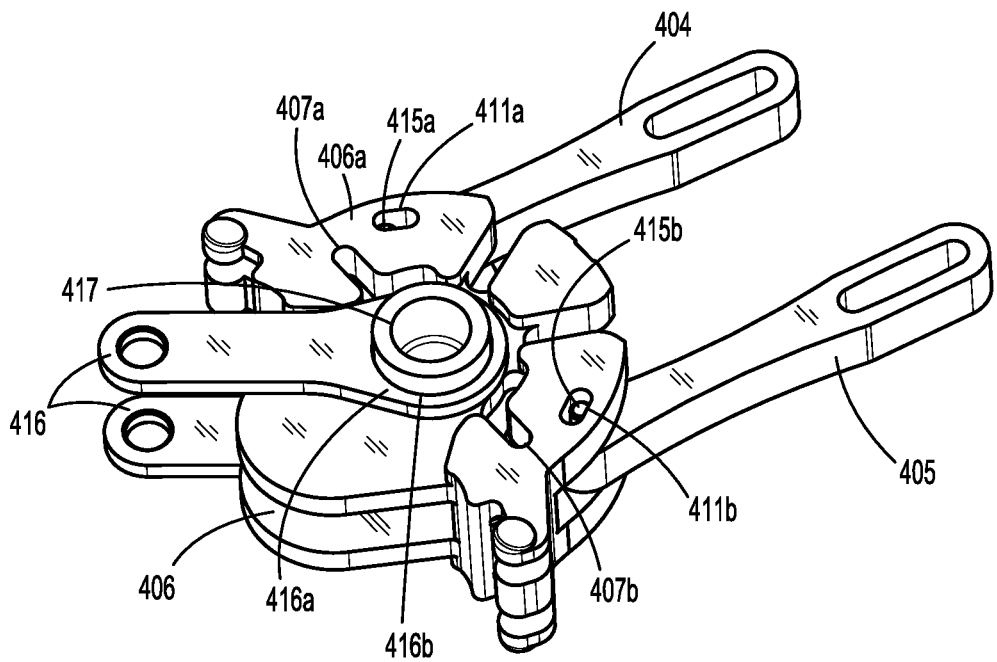
FIG. 8 is a perspective view of the drive conversion assembly of FIG. 7 with a coupling portion of a cam wheel removed.

With particular reference to FIGS. 7 and 8, drive conversion assembly 400 further includes a cam wheel 406 including a base portion 406a and a coupling portion 406b. Base portion 406a of cam wheel 406 defines camming slots 407a, 407b. Each camming slot 407a, 407b may define an L-shape extending transversely outward. Camming slots 407a, 407b of base portion 406a are configured to receive camming pins 409a, 409b (FIG. 6) coupled with respective first and second blade drive members 480, 482 (FIG. 6). Camming pins 409a, 409b extend through respective camming slots 407a, 407b of base portion 406a and further slidably engage respective slots 417a, 417b defined in coupling portion 406b of cam wheel 406. In particular, slots 417a, 417b of coupling portion 406b of cam wheel 406 may be defined on opposing lateral sides of coupling portion 406b and may extend distally inward. Coupling portion 406b may be supported in housing 102 (FIG. 6) by support rods 455 (FIG. 9), which may include biasing members 455a.

Figure 9:
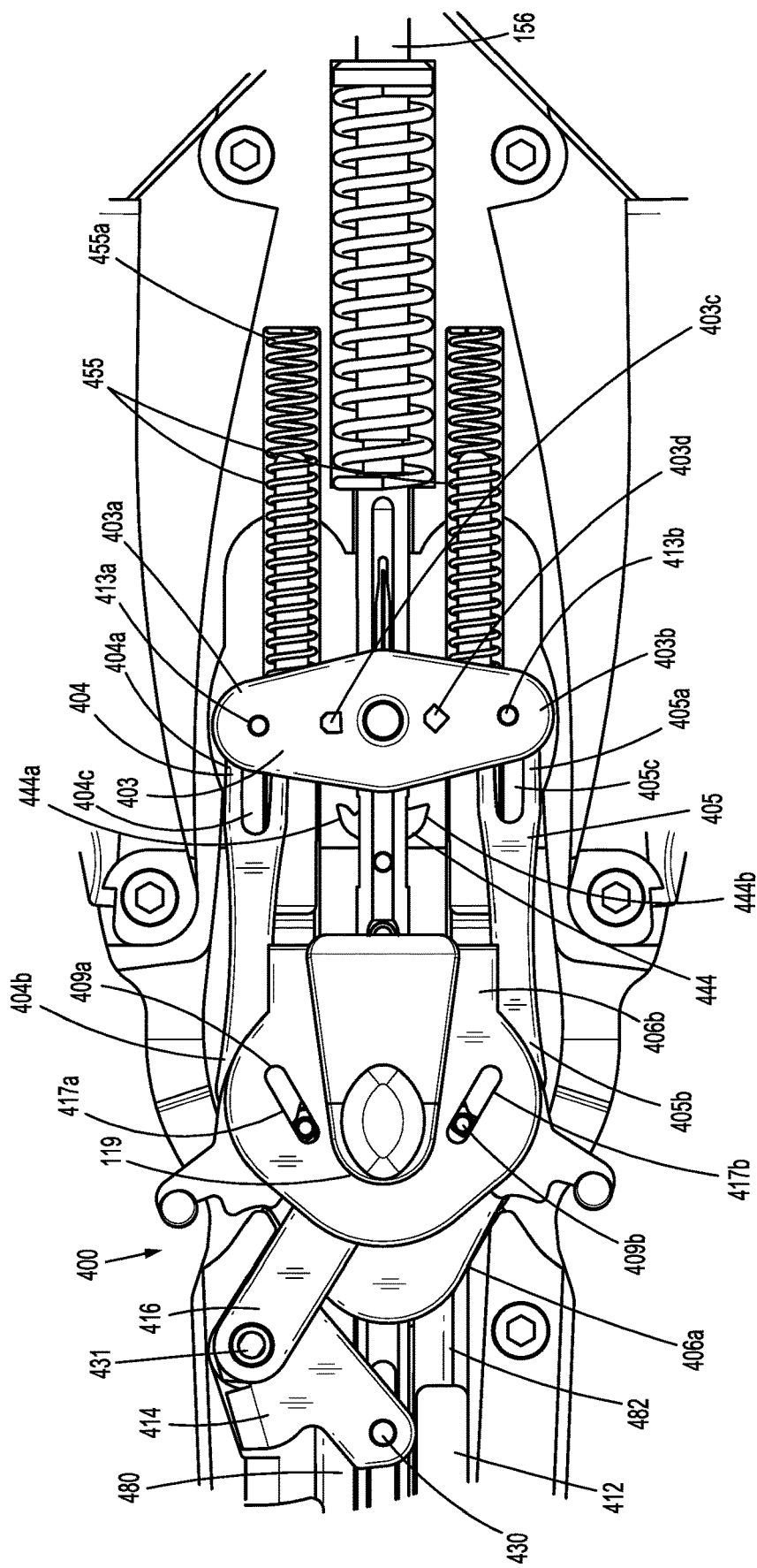
FIG. 9 is a partially enlarged view of the handle assembly of FIG. 6.
Figure 10A:
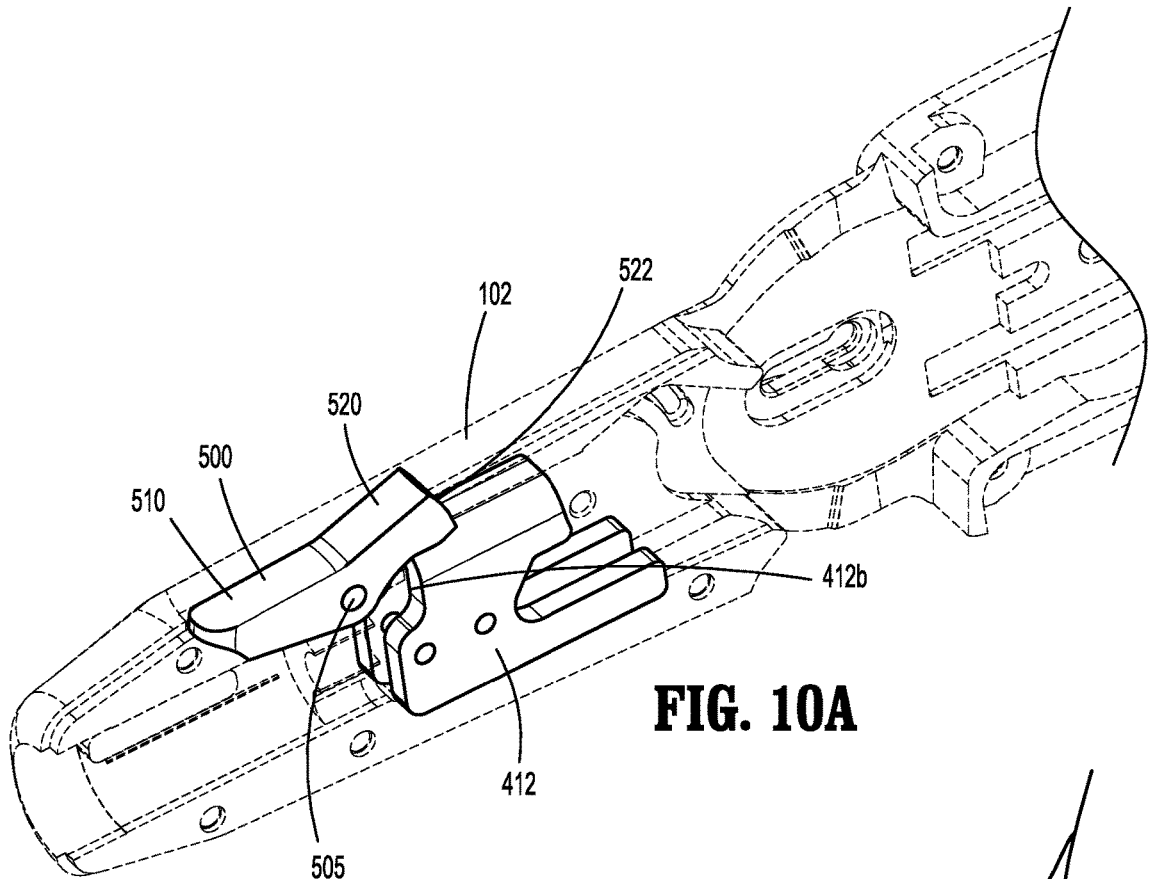
FIGS. 10A-10D are partial perspective views of the handle assembly of FIG. 6, illustrating operation of an unloading lock.
Figure 10B:
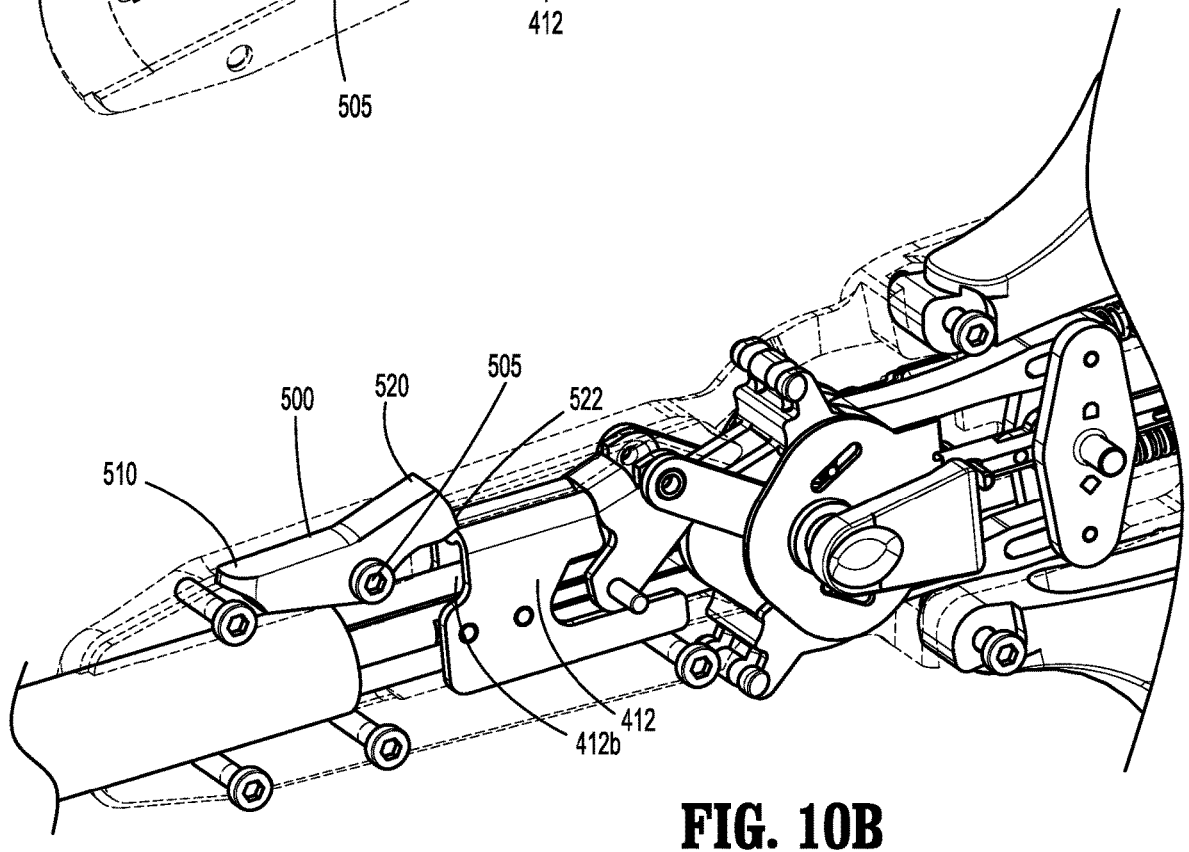
Figure 10C:
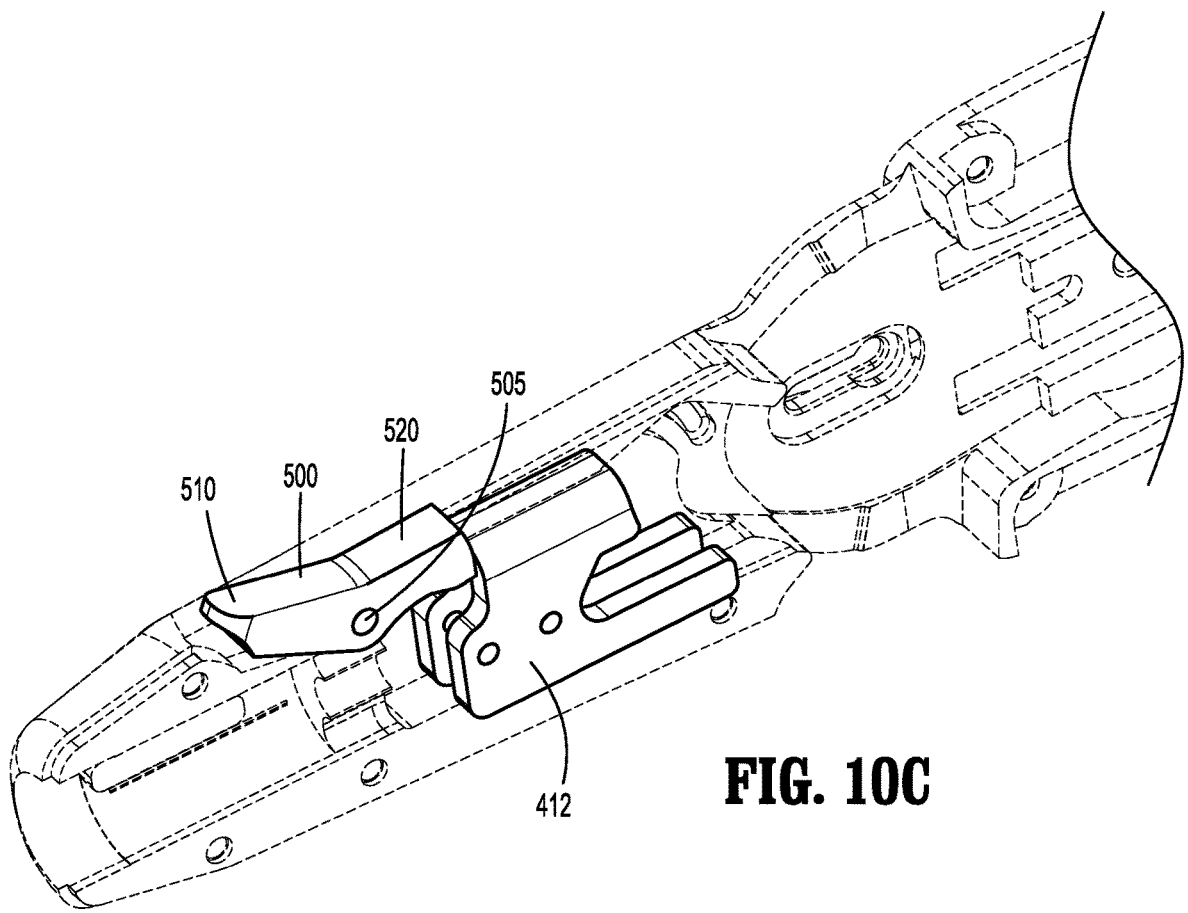
Figure 10D:
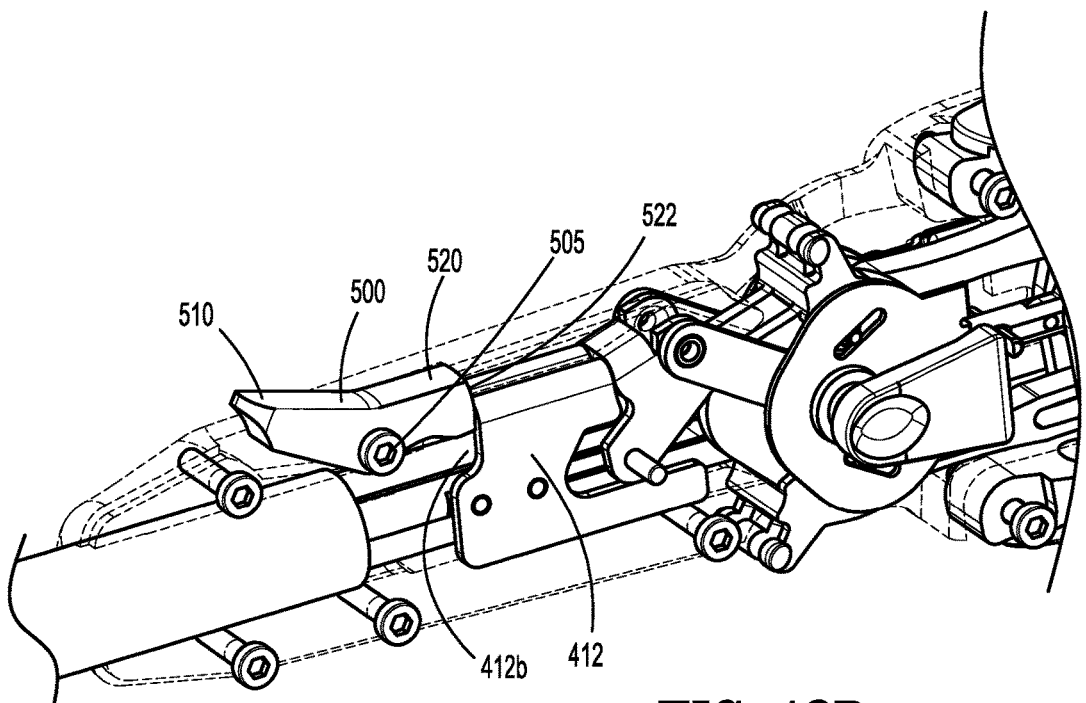

With reference to FIG. 9, drive conversion assembly 400 further includes links 404, 405 and a pivot block 403 rotatable relative to main rod 156. Each link 404, 405 includes a respective proximal portion 404a, 405a and a respective distal portion 404b, 405b. Proximal portions 404a, 405a of links 404, 405 define respective slots 404c, 405c. Each slot 404c, 405c of links 404, 405 is configured to slidably receive a pin 413a, 413b secured to one of laterally opposing sides 403a, 403b of pivot block 403. Distal portions 404b, 405b of links 404, 405 include respective pins 415a, 415b (FIG. 8). Pin 415a is configured to slidably engage camming slot 411a (FIG. 8) defined in base portion 406a of cam wheel 406, and pin 415b is configured to slidably engage camming slot 411b of base portion 406a.

With continued reference to FIG. 9, drive conversion assembly 400 further includes a pawl 444 biased toward a neutral position in which opposing sides 444a, 444b of pawl 444 extend transversely outward from main rod 156 toward respective links 404, 405. Pawl 444 is configured to engage one of pins 403c, 403d of pivot block 403 depending on the orientation of pivot block 403, when main rod 156 is advanced proximally, in order to rotate pivot block 403, thereby providing reciprocating axial displacement of links 404, 405 in opposite directions. Reciprocating axial displacement of links 404, 405 causes rotation of base portion 406a of cam wheel 406, which, in turn, causes reciprocating axial displacement of first and second blade drive members 480, 482 coupled to respective blades 150, 152 (FIG. 5) of tool assembly 120.

With reference now to FIGS. 10A-10D, unloading lock 500 is pivotably secured with housing 102 about a pivot 505. Unloading lock 500 is transitionable between a disengaged position (FIGS. 10A and 10B) in which pusher 412 is axially movable to a distal-most position, and an engaged position (FIGS. 10C and 10D) in which unloading lock 500 engages pusher 412 to inhibit distal movement of pusher 412, which, in turn, inhibits opening of jaws 130, 132. Unloading lock 500 includes a first portion 510 and a second portion 520 defining a curvature such that when unloading lock 500 is in the disengaged position, first portion 510 may be flush with housing 102 and second portion 520 may protrude from housing 102. When unloading lock 500 is in the engaged position, second portion 520 may be flush with housing 102 and first portion 510 may protrude from housing 102. Second portion 520 of unloading lock 500 includes an engaging portion 522 configured to engage a second cutout 412b of pusher 412. When unloading lock 500 is in the disengage position, pusher 412 is biased towards a distal-most position in which engaging portion 522 is proximal (FIG. 10A) of second cutout 412b of pusher 412. Under such a configuration, second cutout 412b of pusher 412 needs to be placed proximal of engaging portion 522 prior to transitioning unloading lock 500 to the engaged position, which can be done by squeezing handles 110 to move main rod 156 proximally.

Figures 12, 12A:
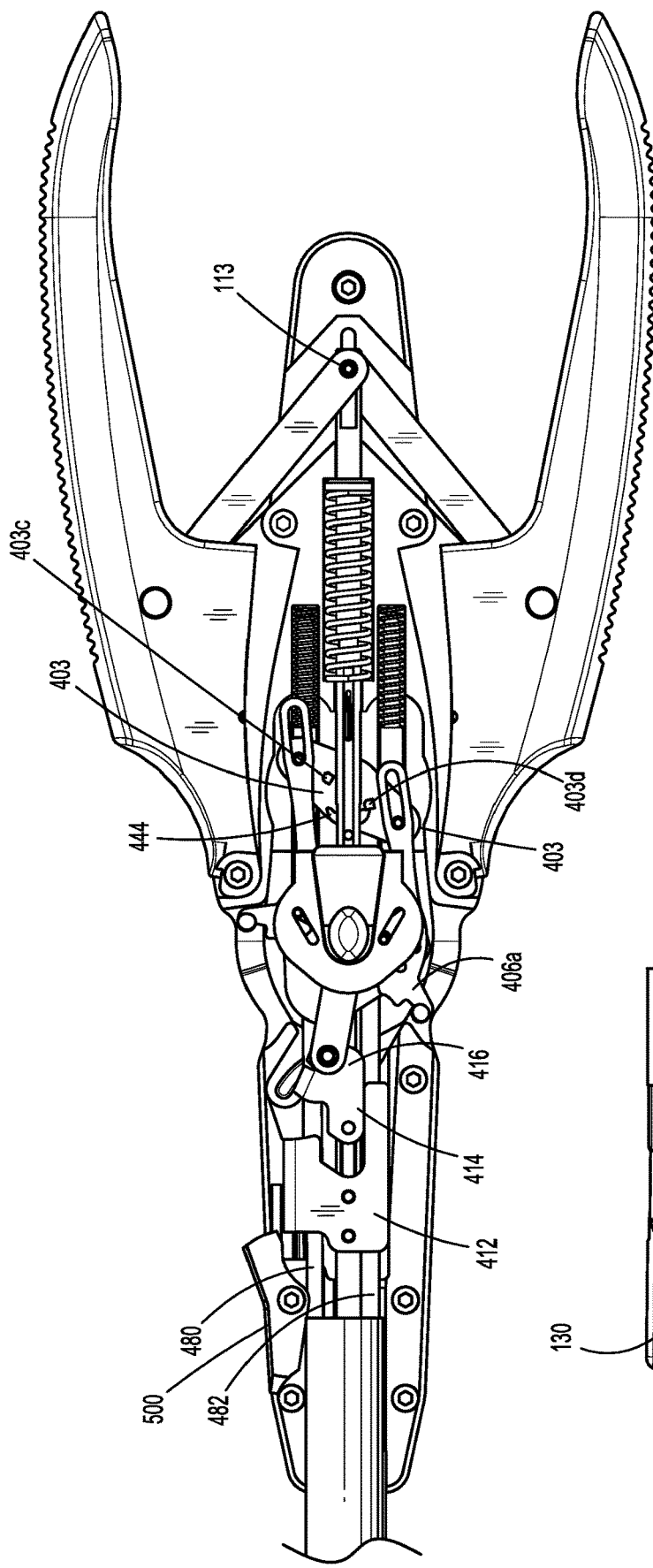
FIGS. 12 and 12A are partial top views of the stitching device of FIG. 1, illustrating the jaws in an approximated position.
Figure 13:
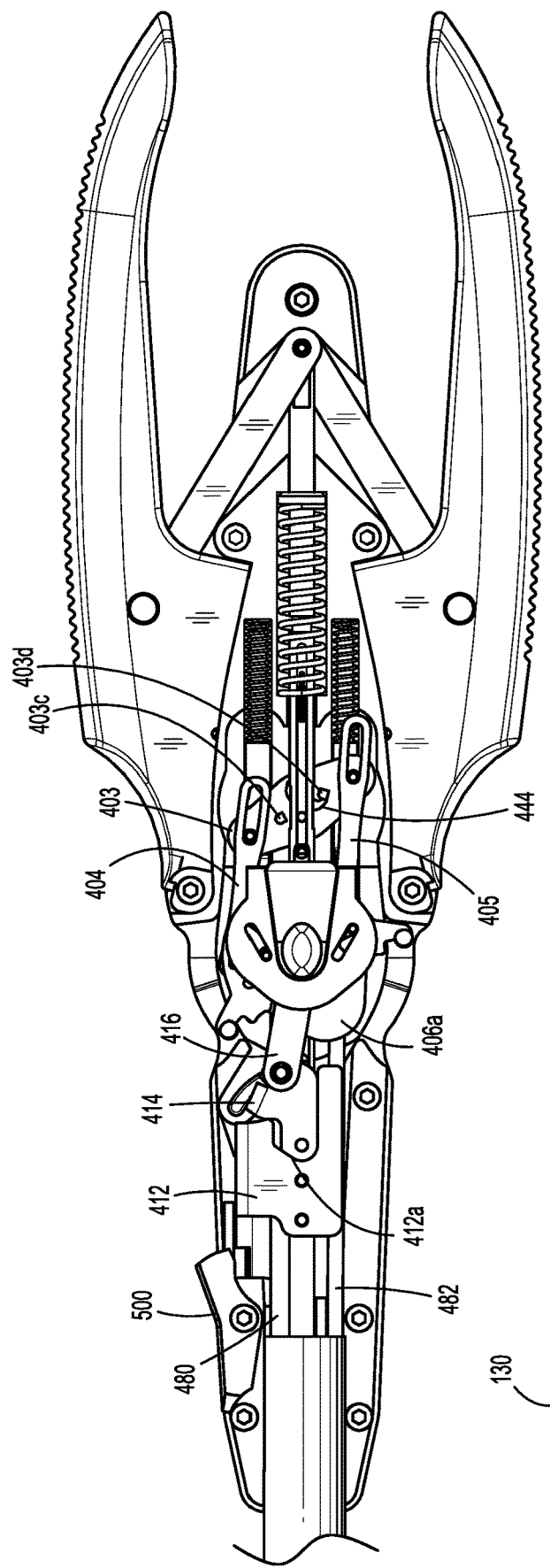
FIGS. 13 and 13A are partial top views of the stitching device of FIG. 1, illustrating swapping of the needle from a first blade to a second blade.
Figure 13A:
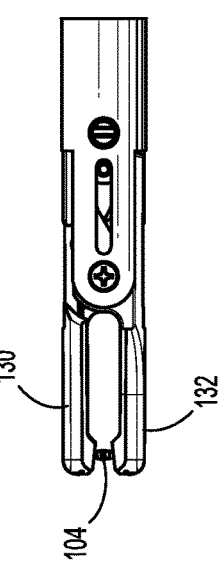

With reference now to FIGS. 11-14, initially, handles 110 are released and jaws 130, 132 are in an open position. In order to close jaws 130, 132 and swap needle 104 between jaws 130, 132, handles 110 are squeezed and main rod 156 coupled to handles 110 is displaced in the direction of arrow "p". Axial displacement of main rod 156 in the proximal direction transitions jaws 130, 132 to the closed position. If needed, jaws 130, 132 can be opened again by releasing handles 110 and needle 104 will stay in the same jaw prior to the reversal process. Continued axial displacement of main rod 156 positions pusher 412 to engage link 414. At this time, pawl 444 approaches pivot block 403, which begins the reversal process. With particular reference to FIGS. 12-13A, continued squeezing of handles 110 positions link 414 in cutout 412a of pusher 412. At this time pawl 444 engages pin 403d (FIG. 12) to rotate pivot block 403, which, in turn, causes reciprocating axial displacement of links 404, 405. The reciprocating axial displacement of links 404, 405 causes rotation of base portion 406a of cam wheel 406. As a result, first and second blade drive members 480, 482 are axially displaced in opposite directions, which, in turn, causes reciprocating axial displacement of blades 150, 152 (FIG. 5) of tool assembly 120.

Figure 14:
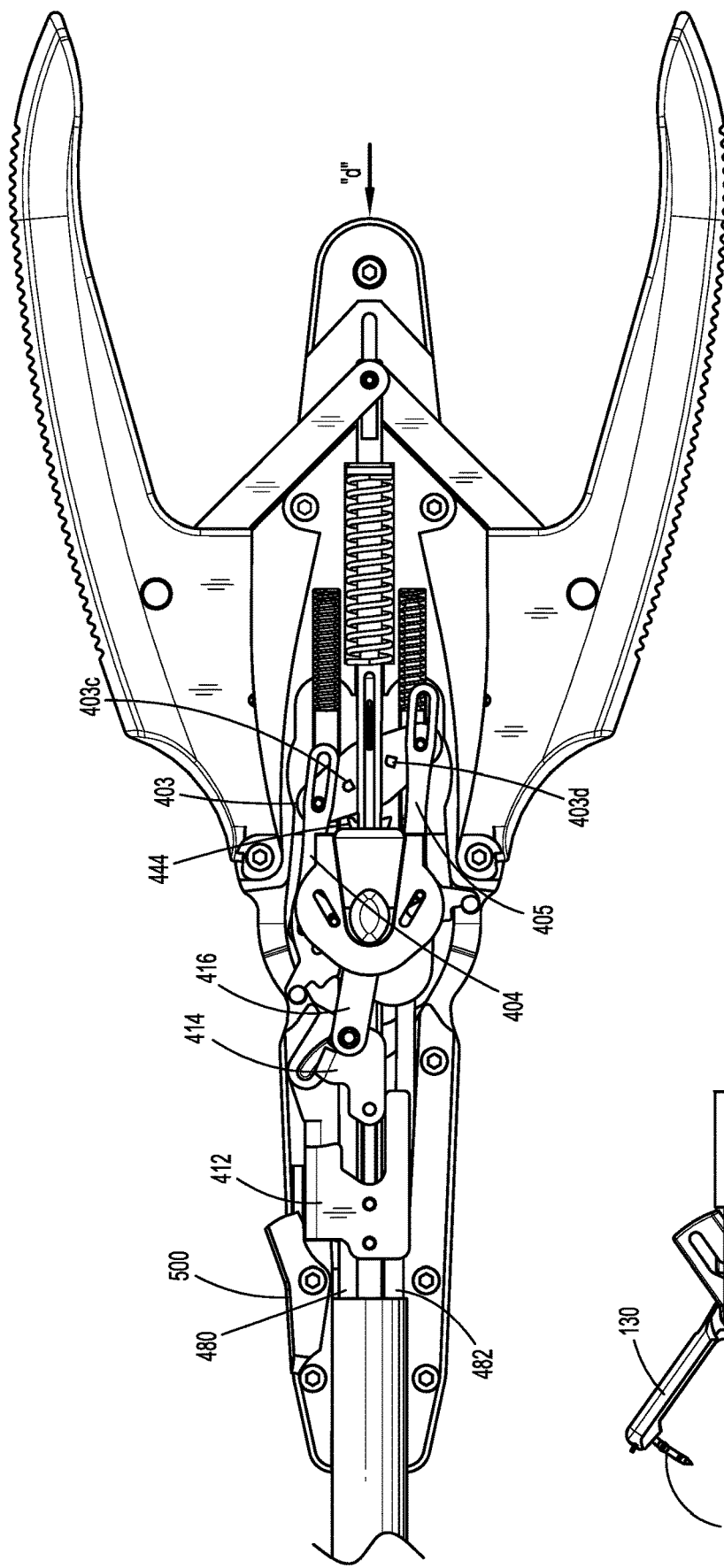
FIGS. 14 and 14A are partial top views of the stitching device of FIG. 1, illustrating the jaws in an open position with the needle supported on the second jaw.
Figure 14A:
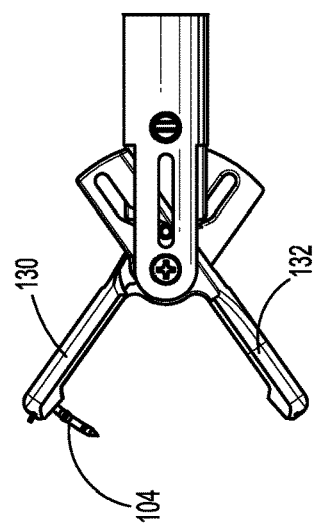

With reference to FIG. 14, at this time, handles 110 can be released to open jaws 130, 132 and retract main rod 156 to the initial position in the direction of arrow "d". When main rod 156 is retracted to the initial position, pawl 444 is moved away from pivot block 403, while pivot block 403 maintains its orientation. At this time, handles 110 may be squeezed to reverse the position of blades 150, 152. Squeezing of handles 110 at this time, advances main rod 156 proximally in the direction of arrow "p" (FIG. 11), which, in turn, causes pawl 444 to this time engage pin 403c of pivot block 403 and rotate pivot block 403 such that links 404, 405 are displaced relative to each other in opposite directions. As discussed, such reciprocating axial displacement of links 404, 405 causes rotation of base portion 406a of cam wheel 406, which, in turn, results in reciprocating axial displacement of first and second blade drive members 480, 482 in opposite directions. In this manner, blades 150, 152 may be displaced in opposite directions to swap needle 104 between jaws 130, 132. Under such a configuration, axial displacement of main rod 156 transitions jaws 130, 132 between the open and closed positions, and axially advances blades 150, 152 of tool assembly 120 in opposite directions, which eliminates the need for a manually operated toggle mechanism.

Figure 15:
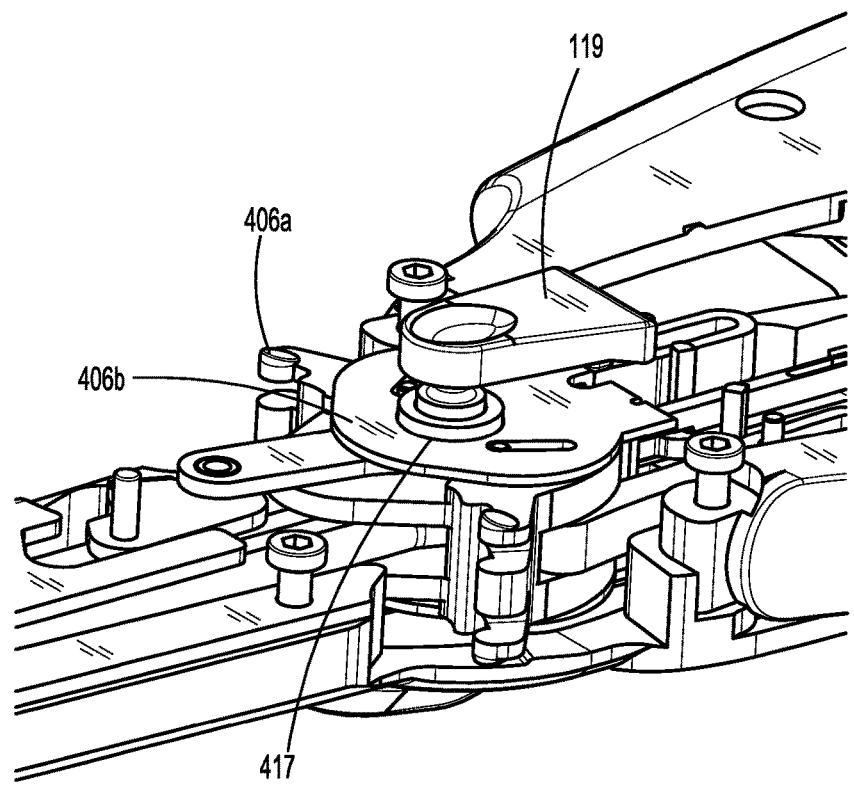
FIG. 15 is a perspective view of the drive conversion assembly of FIG. 6, illustrating a slider operatively coupled with the drive conversion assembly.
Figure 16:
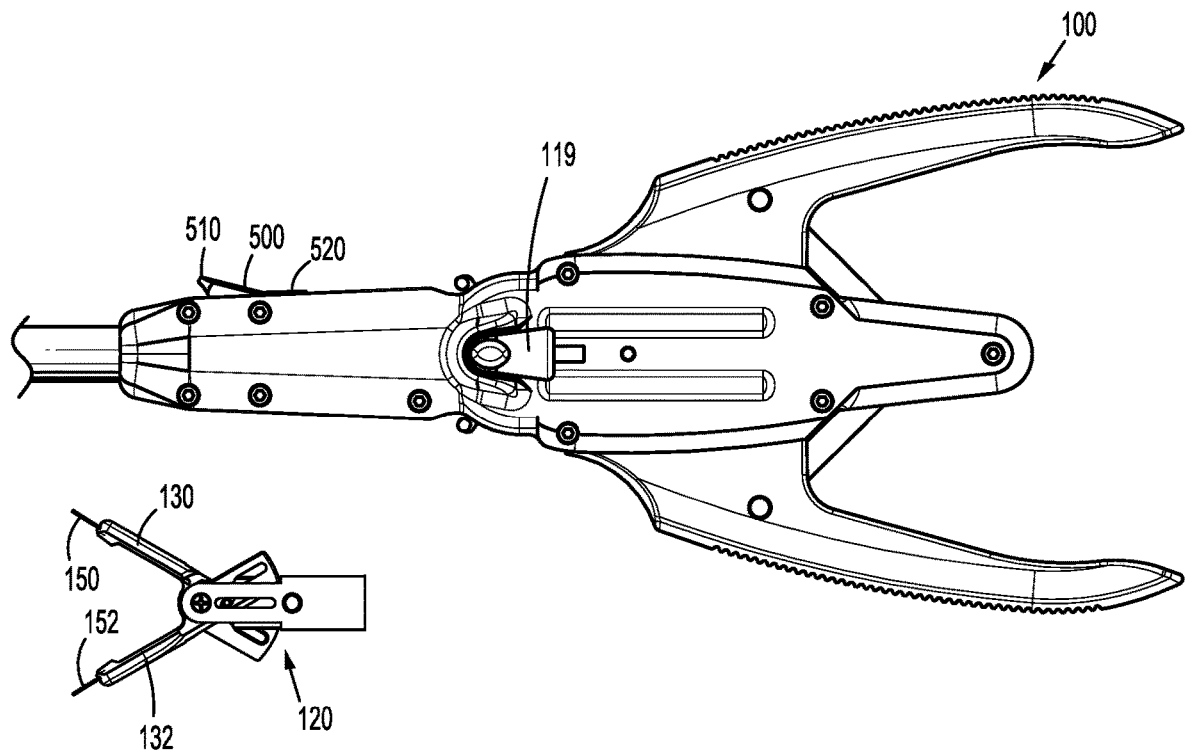
FIG. 16 is a partial top view of the stitching device of FIG. 1, illustrating a reload mode.
Figure 17A:
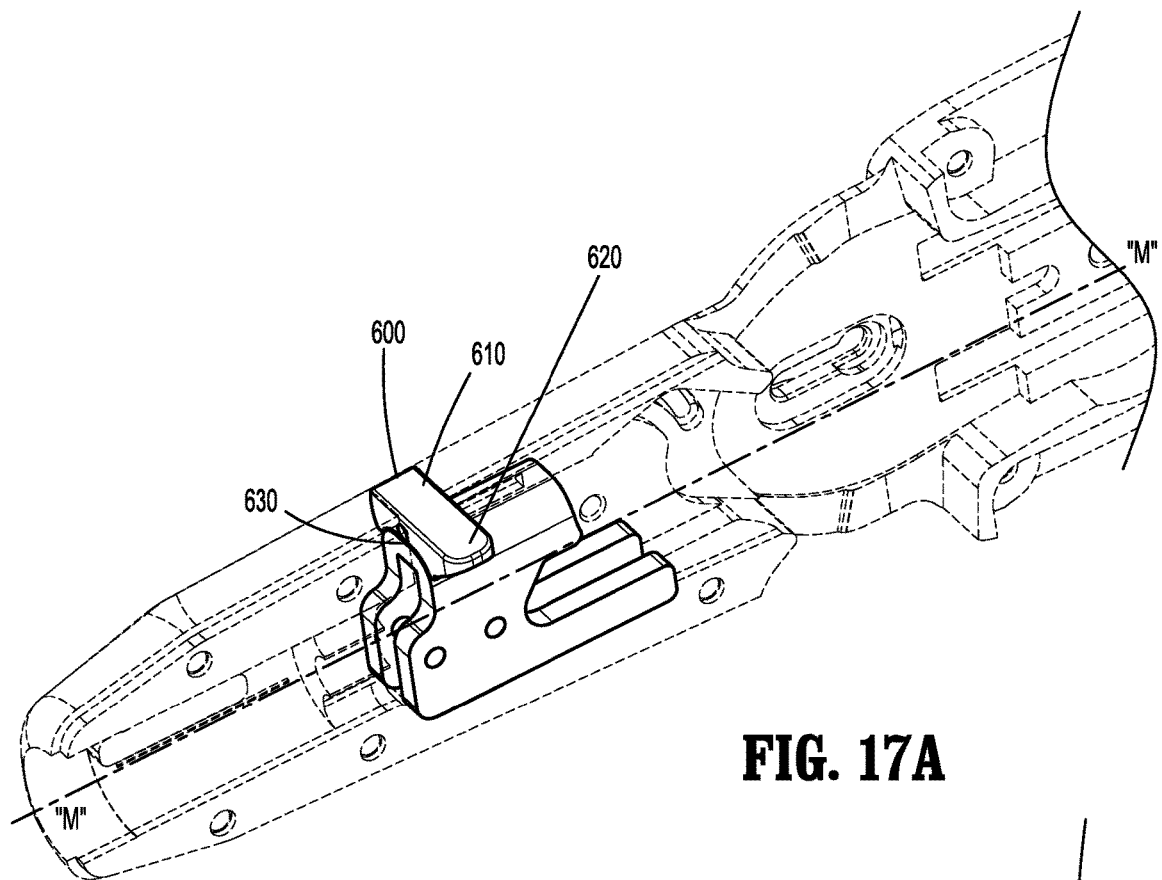
FIGS. 17A-17D are partial perspective views of the handle assembly of FIG. 6 including an unloading lock in accordance with an embodiment of the present disclosure, illustrating operation of the unloading lock.
Figure 17B:
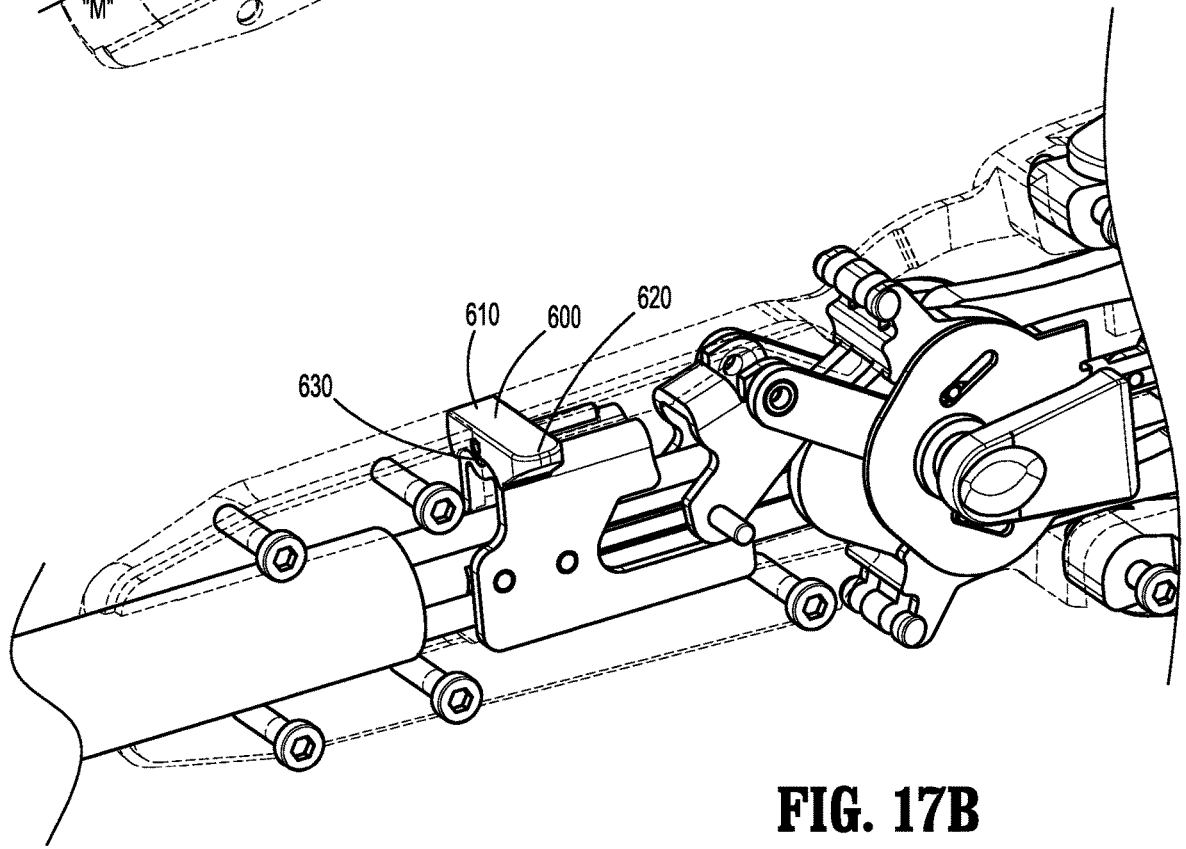
Figure 17C:
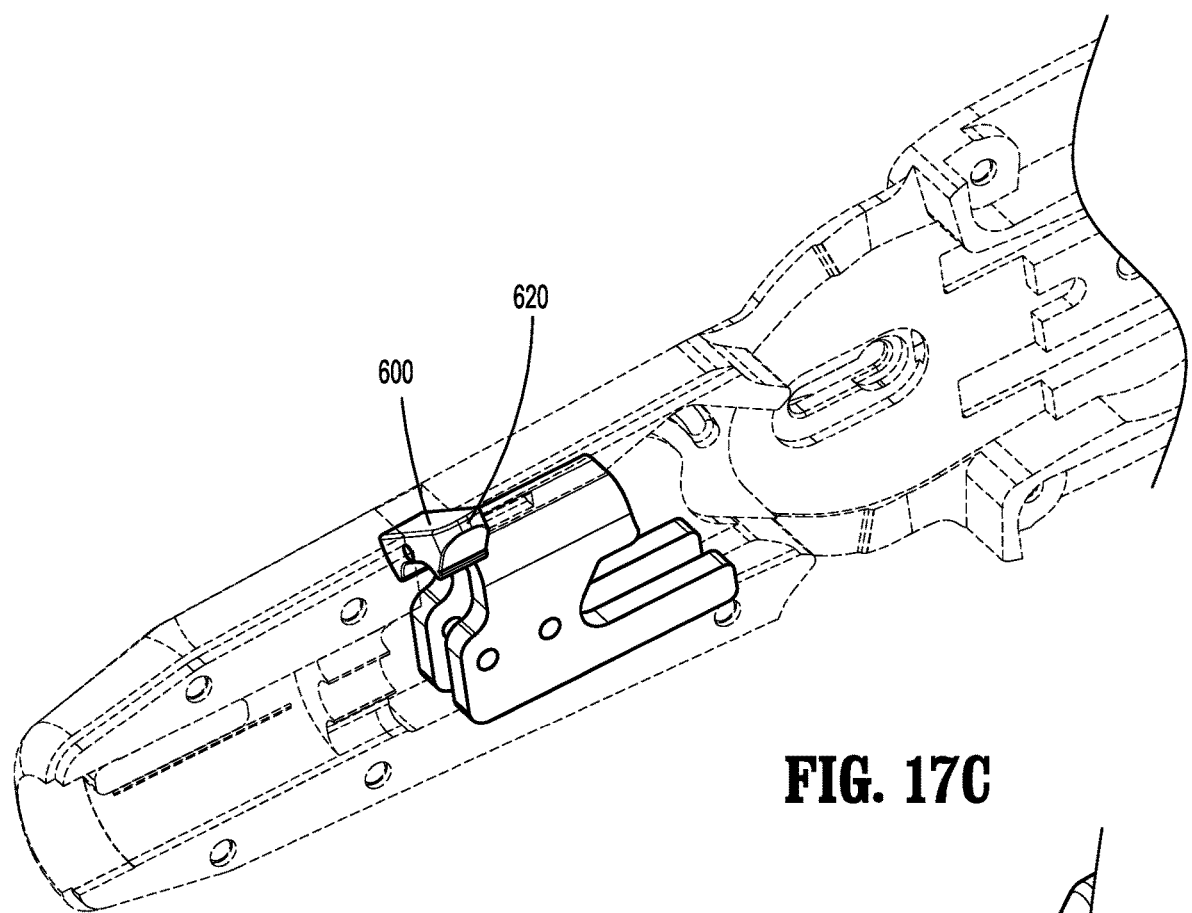
Figure 17D:
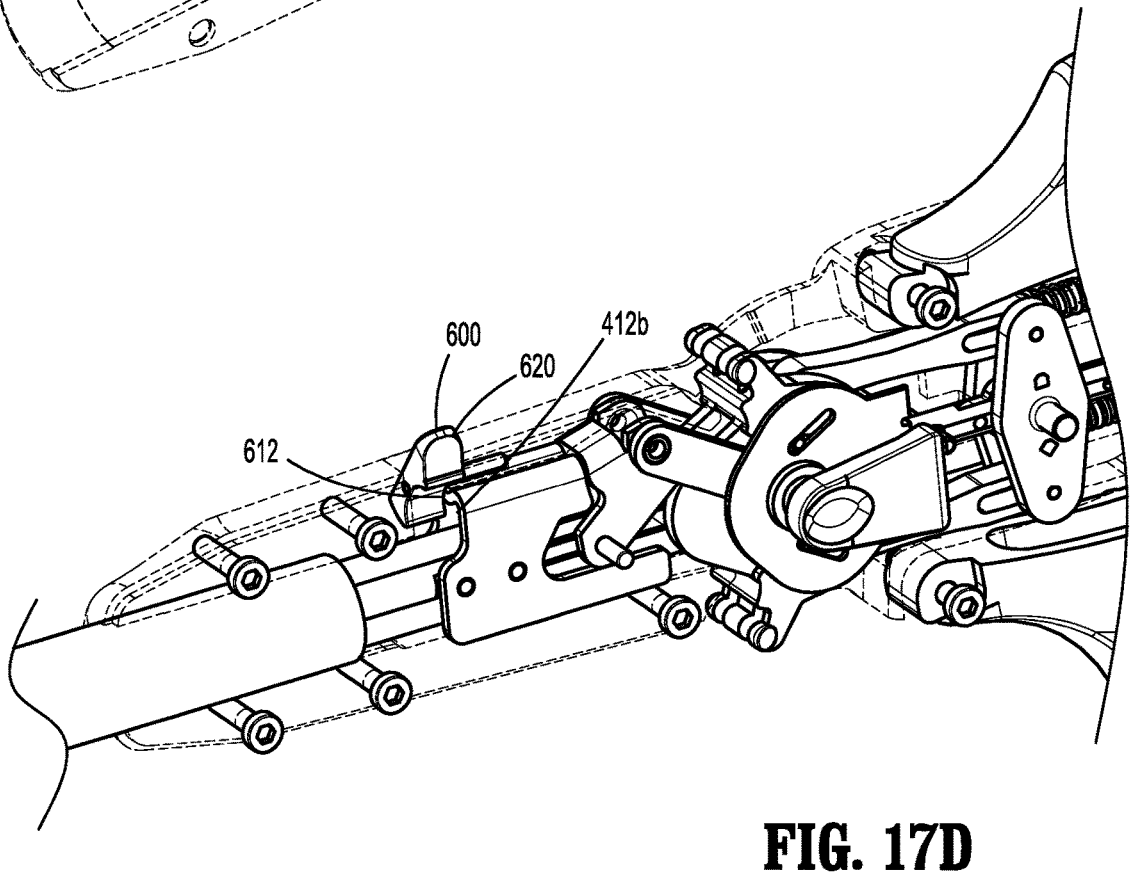
Figure 18A:
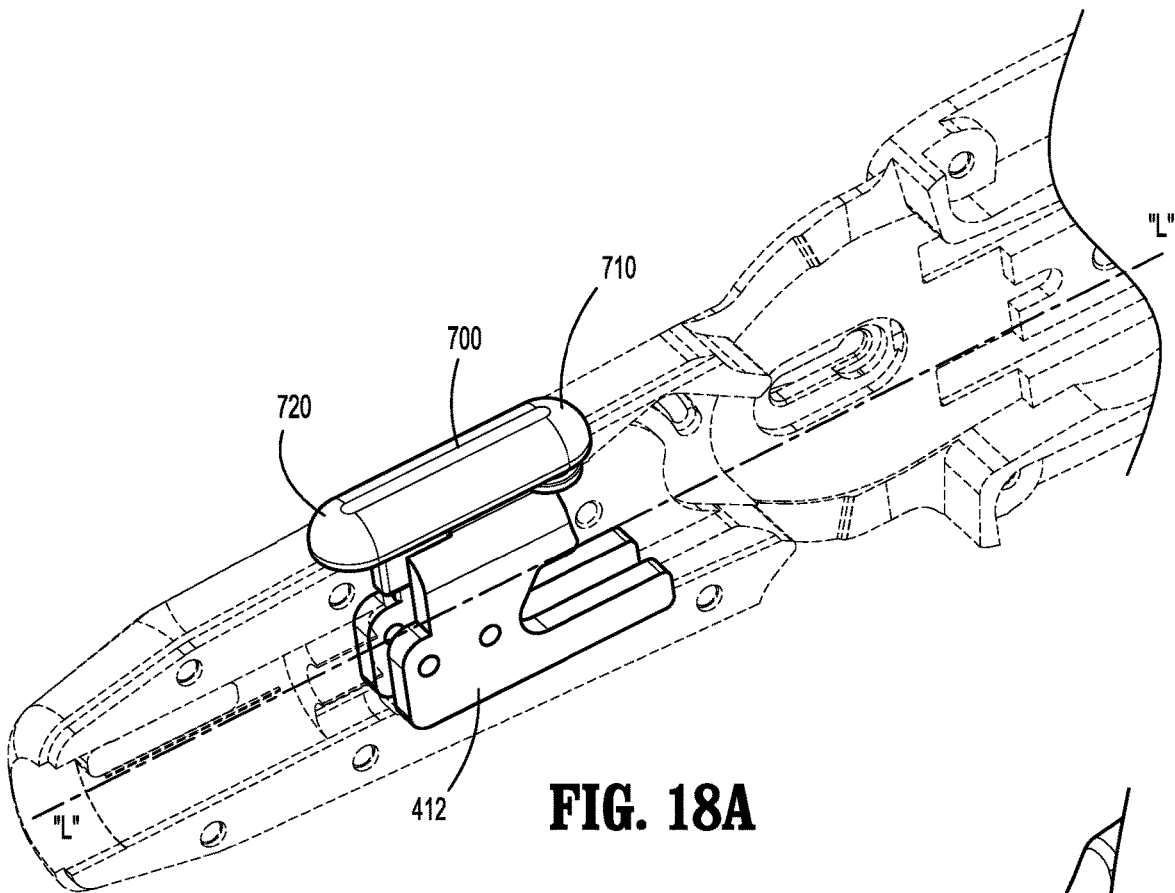
FIGS. 18A-18D are partial perspective views of the handle assembly of FIG. 6 including an unloading lock in accordance with an embodiment of the present disclosure, illustrating operation of the unloading lock.
Figure 18B:
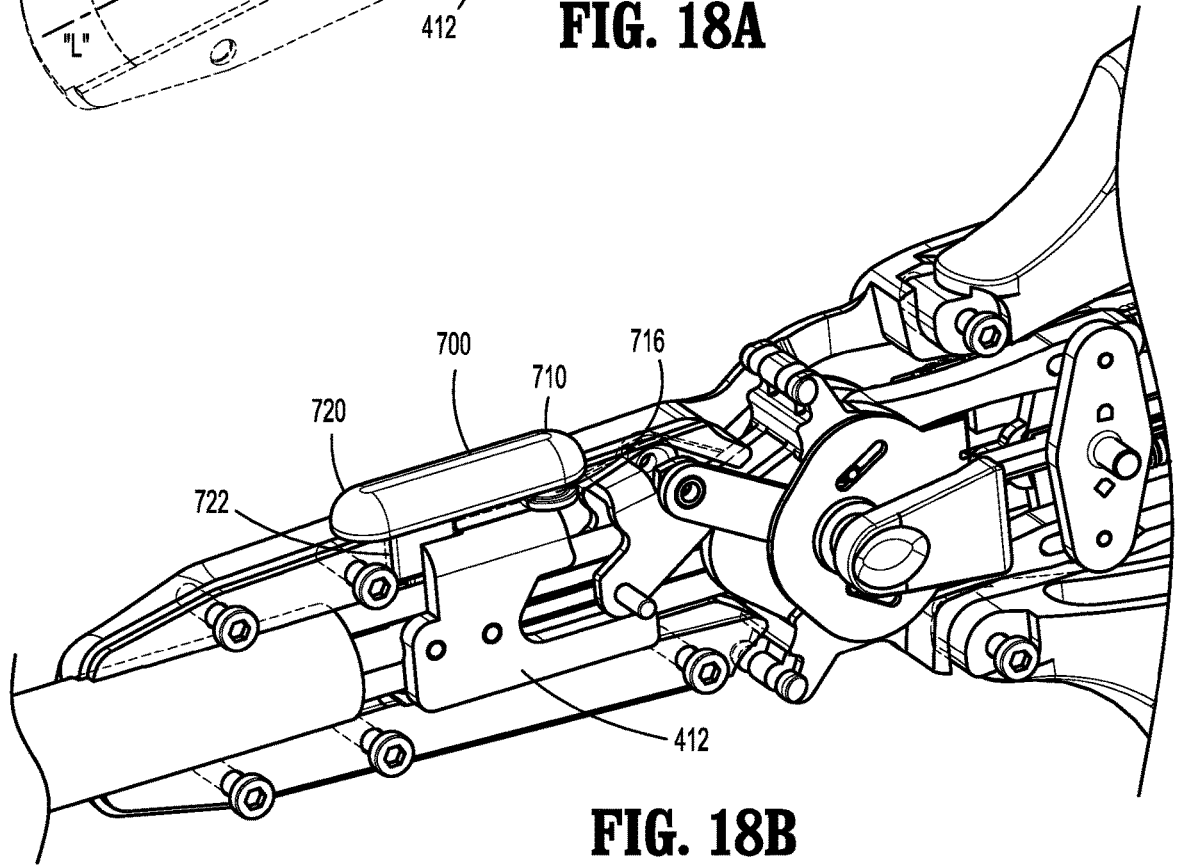
Figure 18C:
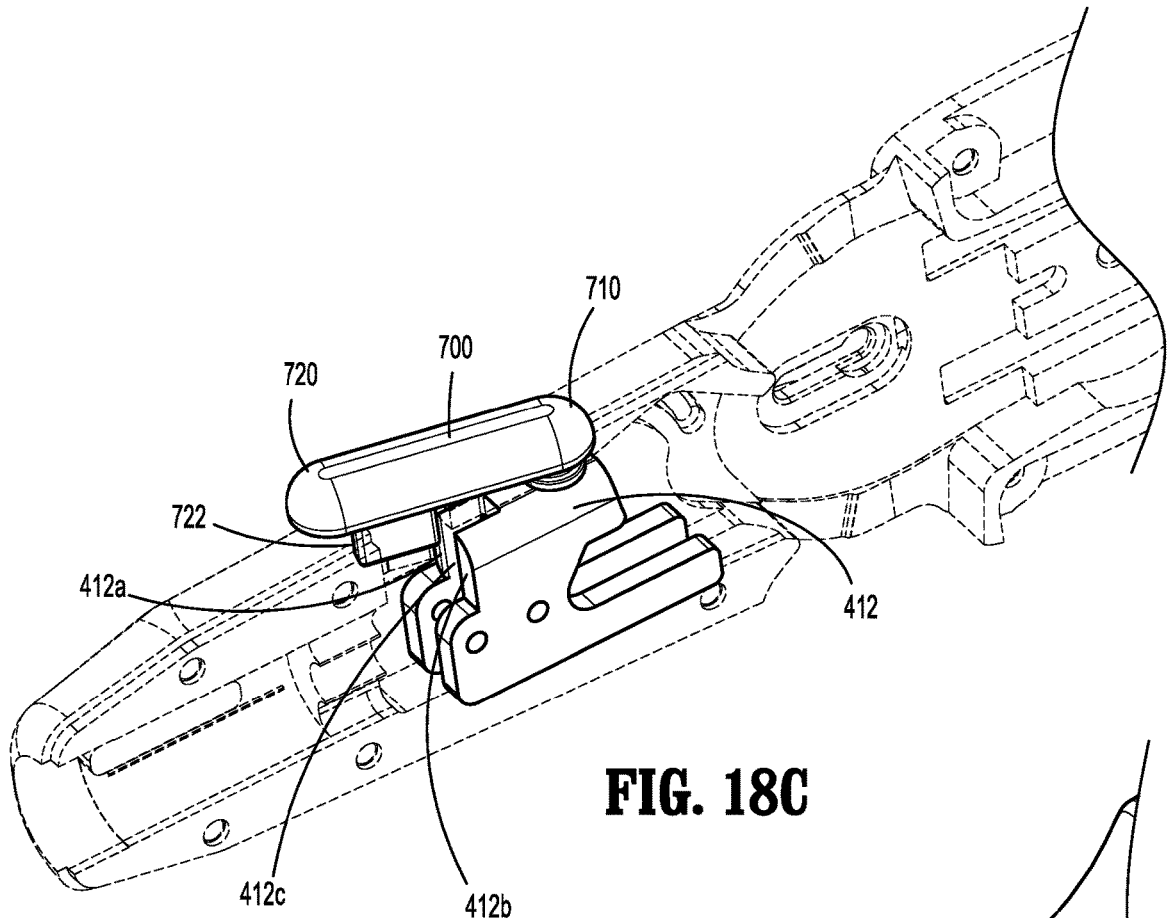
Figure 18D:
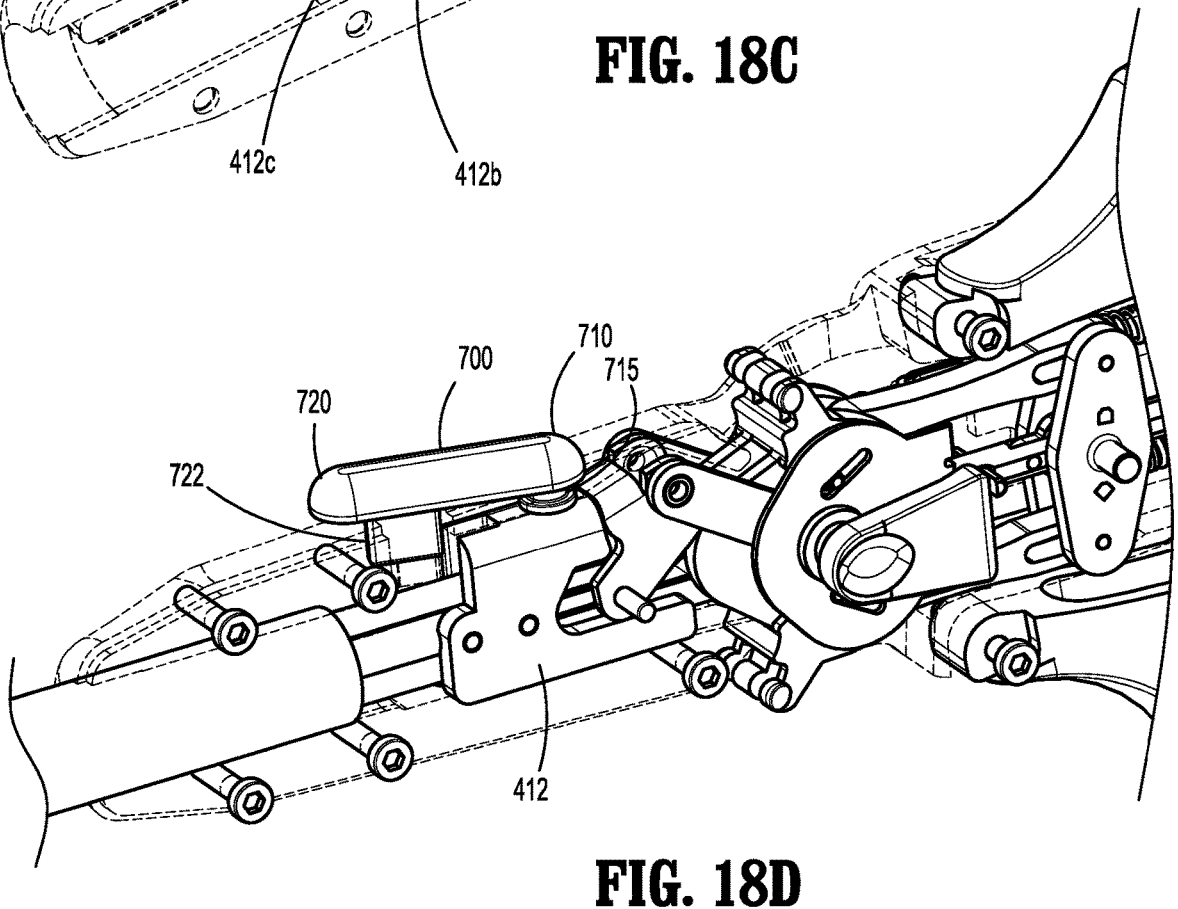

With reference now to FIGS. 15 and 16, handle assembly 100 further includes a slider 119 operatively coupled with drive conversion assembly 400. When slider 119 is pressed, slider 119 engages a protrusion 417 (FIG. 8) on base portion 406a of cam wheel 406 such that axial displacement of slider 119 causes concomitant displacement of cam wheel 406. While slider 119 is pressed, slider 119 may be moved proximally to place stitching device 1000 in the suture mode and distally to place stitching device 1000 in the reload mode. In the reload mode, a reversal mechanism of blades 150, 152 is disabled to inhibit reciprocating axial displacement of blades 150, 152, and to enable a loading of needle 104 into one of jaws 130, 132 or unloading of needle 104 from jaws 130, 132.

Specifically, in the reload mode, links 404, 405 are in a distal position such that both blades 150, 152 are in a distal-most position. In this manner, notches formed in respective blades 150, 152 are aligned with or in registration with respective needle recesses 130a, 132a (FIG. 5) defined in respective jaws 130, 132. With the notches of blades 150, 152 aligned with or in registration with the respective needle recesses 130a, 132a, needle 104 (FIG. 2) may be loaded into a selected one needle recess 130a, 132a of jaws 130, 132 or unloaded from needle recesses 130a, 132 of jaws 130, 132.

In order to place handle assembly 100 in the reload mode, handles 110 are squeezed to move pusher 412 (FIG. 10D) proximally to close jaws 130, 132. Unloading block 500 may be utilized, in order to inhibit opening of jaws 130, 132 prior to releasing of needle 104 from blades 150, 152 during unloading of needle 104. Specifically, the clinician presses second portion 520 of unloading lock 500 such that engaging portion 522 of unloading lock 500 engages second cutout 412b of pusher 412. Under such a configuration, unloading lock 500 inhibits distal movement of pusher 412, thereby keeping jaws 130, 132 closed. At this time, slider 119 may be pressed and pushed distally to place links 404, 405 in the distal-most position. In this manner, notches formed in respective blades 150, 152 are aligned with or in registration with respective needle recesses 130a, 132a (FIG. 5) defined in respective jaws 130, 132. With the notches of blades 150, 152 aligned with or in registration with the respective needle recesses 130a, 132a, unloading lock 500 may be transitioned to the disengaged position by pressing first portion 510 of unloading lock 500, which enables pusher 412 to move distally 412, thereby opening jaws 130, 132. At this time, needle 104 may be removed from needle recesses 130a, 132a of jaws 130, 132. In this manner, unloading lock 500 effects release of needle 104 from blades 150, 152 prior to the opening of jaws 130, 132.

In the suture mode, jaws 130, 132 are in the open position, and needle 104 is loaded and held in one jaw 130 or 132. Jaws 130, 132 may be positioned about or over a target tissue and handles 110 may be actuated to approximate jaws 130, 132. As jaws 130, 132 are approximated, the exposed end of needle 104 is penetrated through the target tissue and enters opposed jaw 130 or 132. With needle 104 in opposed jaw 130 or 132, pawl 444 rotates pivot block 403, which, in turn, causes reciprocating axial displacement of links 404, 405. The reciprocating axial displacement of links 404, 405 causes rotation of base portion 406a. As a result, first and second blade drive members 480, 482 are axially displaced in opposite directions, which, in turn, causes reciprocating axial displacement of blades 150, 152 (FIG. 5) of tool assembly 120. In so doing, needle 104 is swapped from one blade 150 or 152 to the other blade 150 or 152, and thus, loaded or held in the other jaw 130 or 132.

In use, stitching device 1000 is transitioned to the reload mode by squeezing handles 110 and sliding slider 119 (FIG. 16) distally. In this manner, first and second blade control members 480, 482 are placed in a distal position such that both blades 150, 152 (FIG. 5) are in a distal-most position. At this time, notches formed in respective blades 150, 152 are aligned with or in registration with respective needle recesses 130a, 132a (FIG. 5) defined in respective jaws 130, 132. With the notches of blades 150, 152 aligned with or in registration with the respective needle recesses 130a, 132a (FIG. 5) of respective jaws 130, 132, needle 104 (FIG. 2) may be positioned or loaded into a selected one needle recess 130a, 132a of jaws 130, 132.

Once needle 104 is loaded into one of the needle recesses 130a, 132a (FIG. 5) of jaws 130, 132, slider 119 is moved proximally to transition stitching device 1000 to the suture mode. At this time, each blade 150, 152 engages a respective groove 104a of needle 104. With needle 104 engaged by both blades 150, 152, handles 110 are actuated so that only one blade 150, 152, is in engagement with needle 104 (FIG. 5), and the other blade 150, 152 is disengaged from needle 104.

With jaws 130, 132 in the open position and needle 104 loaded and held in one jaw 130 or 132, jaws 130, 132 may be positioned about or over a target tissue. In order to close jaws 130, 132 and swap needle 104 between jaws 130, 132, handles 110 are squeezed. Main rod 156 coupled to handles 110 is displaced in the direction of arrow "p", which transitions jaws 130, 132 to the closed position (FIG. 12A). As jaws 130, 132 are approximated, the exposed end of needle 104 is penetrated through the target tissue and enters opposed jaw 130 or 132. With needle 104 in opposed jaw 130 or 132, continued squeezing of handles 110 positions link 414 in cutout 412a of pusher 412. At this time pawl 444 rotates pivot block 403, which, in turn, causes reciprocating axial displacement of links 404, 405. The reciprocating axial displacement of links 404, 405 causes rotation of base portion 406a. As a result, first and second blade drive members 480, 482 are axially displaced in opposite directions, which, in turn, causes reciprocating axial displacement of blades 150, 152 (FIG. 5) of tool assembly 120. In so doing, needle 104 is swapped from one blade 150 or 152 to the other blade 150 or 152, and thus, loaded or held in the other jaw 130 or 132. With needle 104 being swapped from one blade 150, 152 to another blade 150, 152, handles 110 may be released to thereby open jaws 130, 132 and draw needle 104 through the target tissue. In so doing, the suture is also drawn through the tissue. The process is repeated, passing needle 104 between jaws 130, 132 and drawing the suture through the target tissue, thereby suturing the target tissue as needed or desired.

Needle 104 may be unloaded from jaws 130, 132 to be replaced with a new needle 104 during or after the surgical procedure. In order to replace needle 104, handles 110 are squeezed to move pusher 412 (FIG. 10D) proximally. At this time, the clinician presses second portion 520 of unloading lock 500 such that engaging portion 522 of unloading lock 500 engages second cutout 412b of pusher 412, thereby keeping jaws 130, 132 closed. At this time, slider 119 may be pressed and pushed distally to place links 404, 405 in the distal-most position. In this manner, notches formed in respective blades 150, 152 are aligned with or in registration with respective needle recesses 130a, 132a (FIG. 5) defined in respective jaws 130, 132. With the notches of blades 150, 152 aligned with or in registration with the respective needle recesses 130a, 132a, unloading lock 500 may be transitioned to the disengaged position by pressing first portion 510 of unloading lock 500, thereby opening jaws 130, 132. At this time, needle 104 may be removed from needle recesses 130a, 132a of jaws 130, 132 and a new needle 104 may be loaded into jaws 130, 132.

With reference now to FIGS. 17A-17D, there is illustrated an unloading lock 600 in accordance with another embodiment of the present disclosure for use with stitching device 1000. Unloading lock 600 includes features that are identical to the features described with respect to unloading lock 500. Thus, the identical parts in unloading lock 600 will not be described herein to avoid obscuring the present disclosure in unnecessary detail.

As discussed hereinabove with respect to unloading lock 500, unloading lock 600 is configured to inhibit opening of jaws 130, 132 before needle 104 is released from blades 150, 152 during the unloading process of needle 104.

Unloading lock 600 is pivotally secured with housing 102 about a pivot. Unloading lock 600 is transversely disposed on housing 102 with respect to a longitudinal axis "M-M" defined by handle assembly 100. Unloading lock 600 is transitionable between a disengaged position in which pusher 412 is movable to a distal-most position, and an engaged position in which unloading lock 600 engages pusher 412 to inhibit distal movement of pusher 412, which, in turn, inhibits opening of jaws 130, 132. Unloading lock 600 defines an arcuate recess 630 configured enable distal movement of pusher 412 therethrough when loading lock 600 is in the disengaged position. Unloading lock 600 includes a first portion 610 and a second portion 620. Unloading lock 600 is pivotally coupled with housing 102 such that when unloading lock 600 is in the disengaged position, first and second portions 610, 620 may be flush with housing 102. When unloading lock 600 is in the engaged position, first portion 610 pivots such that an engaging portion 612 of first portion 610 engages second cutout 412b of pusher 412. At this time, second portion 620 extends out of housing 102.

The method of stitching target tissue including unloading of needle 104 from jaws 130, 132 has been described hereinabove and thus will not be described herein to avoid obscuring the present disclosure in unnecessary detail.

With reference now to FIGS. 18A-18D, there is illustrated an unloading lock 700 in accordance with a further embodiment of the present disclosure for use with stitching device 1000. Unloading lock 700 includes features that are identical to the features described with respect to unloading locks 500, 600. Thus, the identical parts in unloading lock 700 will not be described herein to avoid obscuring the present disclosure in unnecessary detail.

As discussed hereinabove with respect to unloading locks 500, 600, unloading lock 700 is configured to inhibit opening of jaws 130, 132 prior to the release of needle 104 from blades 150, 152 during the unloading process of needle 104. Unloading lock 700 is pivotally secured with housing 102 about a pivot 715. Unloading lock 700 is transitionable between a disengaged position in which pusher 412 is movable to the distal-most position, and an engaged position in which unloading lock 700 engages pusher 412 to inhibit distal movement of pusher 412, which, in turn, inhibits opening of jaws 130, 132. In the disengaged position, unloading lock 700 is aligned with a longitudinal axis "L-L" (FIG. 18A) defined by handle assembly 100. In the engaged position, second portion 720 is offset from longitudinal axis "L-L". In particular, second portion 720 includes a finger 722. Pusher 412 includes engaging walls 412a, 412b defining a slot 412c therebetween. Slot 412c is dimensioned to receive finger 722 when unloading lock 700 is in the disengaged position to enable axial displacement of unloading lock 700 to the distal-most position. Engaging walls 412a, 412b are configured to engage finger 722 to inhibit distal movement of pusher 412.

The method of stitching target tissue, including unloading needle 104 from jaws 130, 132, has been described hereinabove and thus will not be described herein to avoid obscuring the present disclosure in unnecessary detail.

Figure 19A:
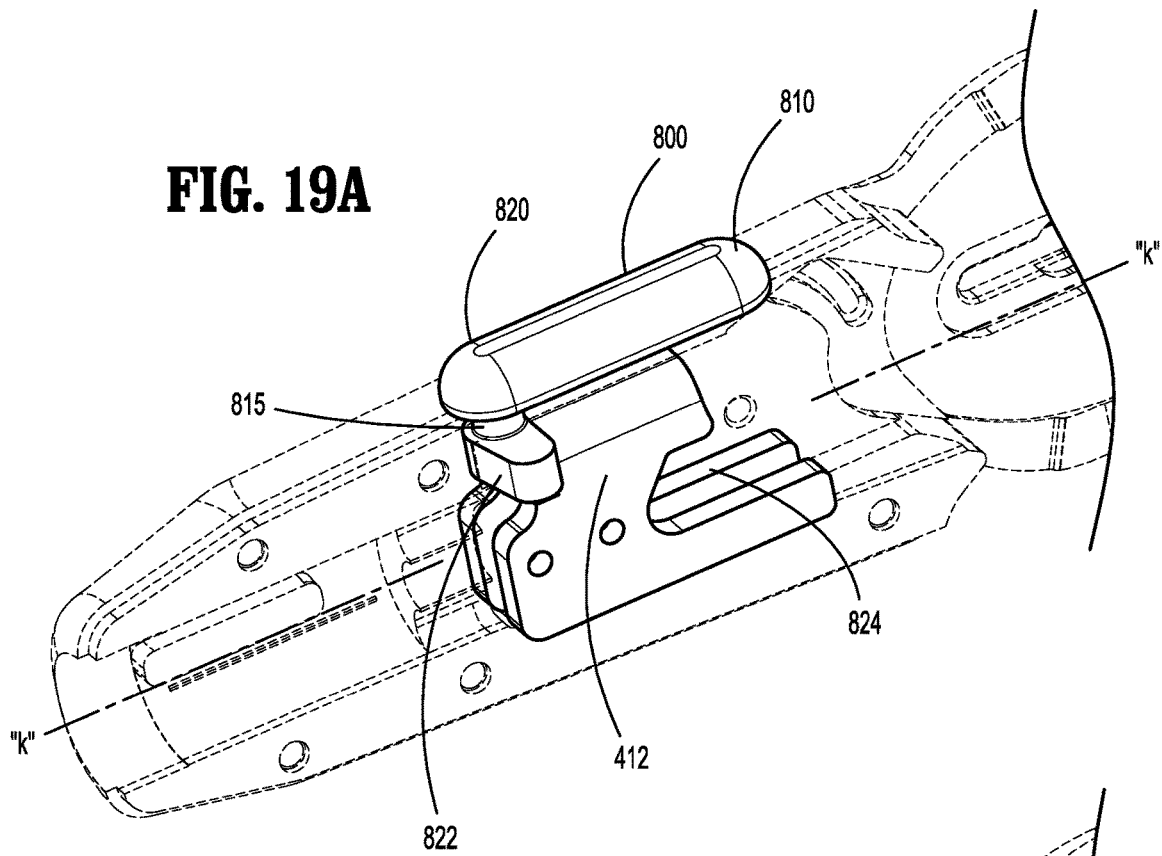
FIGS. 19A and 19B are partial perspective views of the handle assembly of FIG. 6 including an unloading lock in accordance with an embodiment of the present disclosure, illustrating operation of the unloading lock.
Figure 19B:
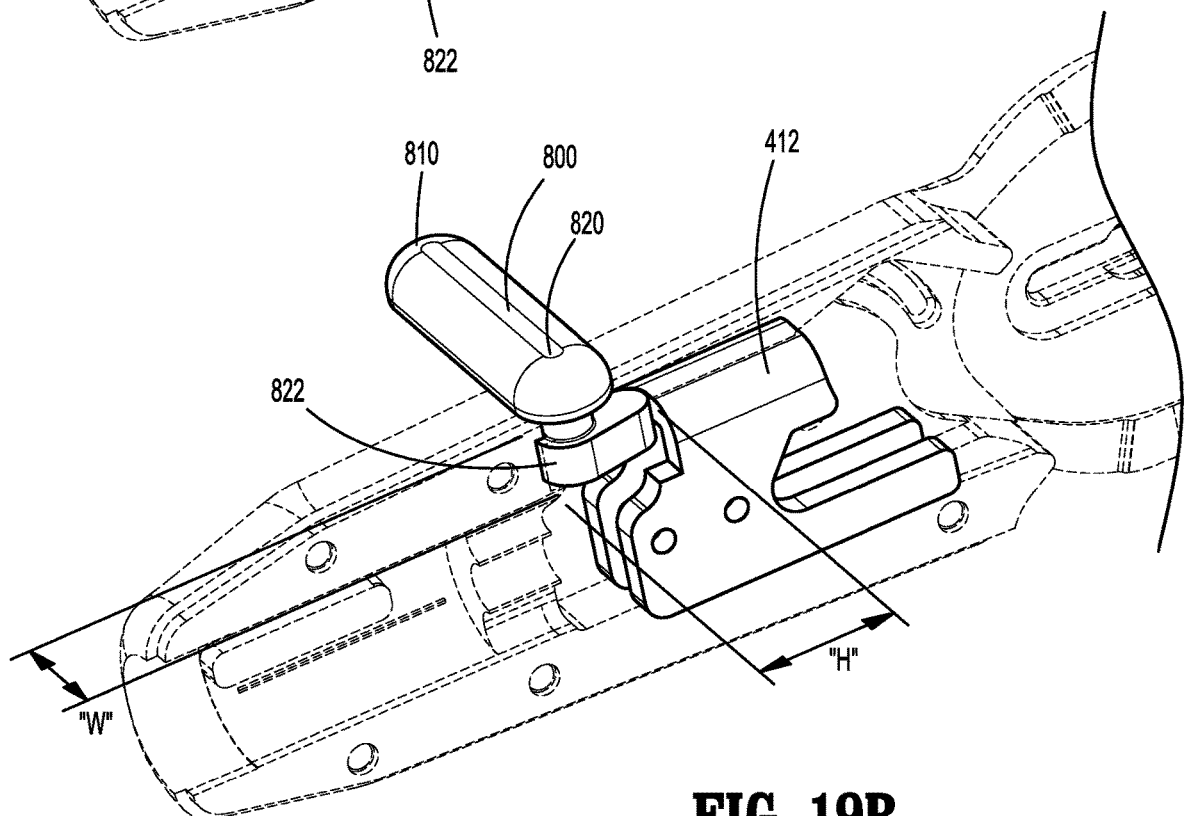

With reference to FIGS. 19A and 19B, there is illustrated an unloading lock 800 in accordance with yet another embodiment of the present disclosure for use with stitching device 1000. Unloading lock 800 includes features that are identical to the features described with respect to unloading locks 500, 600, 700. Thus, the identical parts in unloading lock 800 will not be described herein to avoid obscuring the present disclosure in unnecessary detail.

As discussed hereinabove with respect to unloading lock 700, unloading lock 800 is configured to inhibit opening of jaws 130, 132 prior to the release of needle 104 from blades 150, 152. Unloading lock 800 includes first and second portions 810, 820. In particular, first portion 810 is rotatable about a pin 815 in alignment with second portion 820. Second portion 820 includes a finger 822. First portion 810 and finger 822 are rotatable as a single construct about pin 815. Finger 822 includes a width "W" and a length "H" larger than width "W". In particular, length "H" of finger 822 is transverse to first portion 810.

Unloading lock 800 is transitionable between a disengaged position in which first and second portions 810, 820 are aligned with a longitudinal axis "K-K" defined by handle assembly 100, and an engaged position in which first portion 810 is offset from longitudinal axis "K-K". Under such a configuration, when unloading lock 800 is in the disengaged position, width "W" of finger 822 is aligned with longitudinal axis "K-K", and when unloading lock 800 is in the engaged position, length "H" larger than width "W" is aligned with longitudinal axis "K-K". Under such a configuration, when unloading lock 800 is in the engaged position, length "H" of finger 822 inhibits distal movement of pusher 412, while in the disengaged position, width "W" of finger 822 enables axial movement of pusher 412 to the distal-most position.

The method of stitching target tissue including unloading of needle 104 from jaws 130, 132 has been described hereinabove and thus will not be described herein to avoid obscuring the present disclosure in unnecessary detail.

Figure 20A:
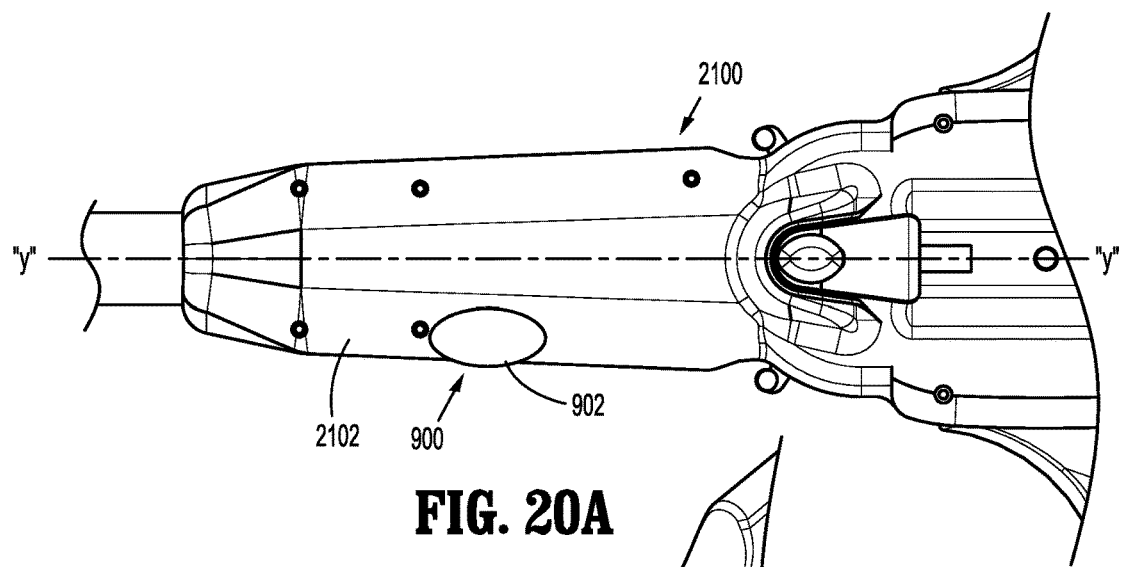
FIG. 20A is a partial top view of a handle assembly including an unloading lock in accordance with another embodiment of the present disclosure for use with the stitching device of FIG. 1.
Figure 20B:
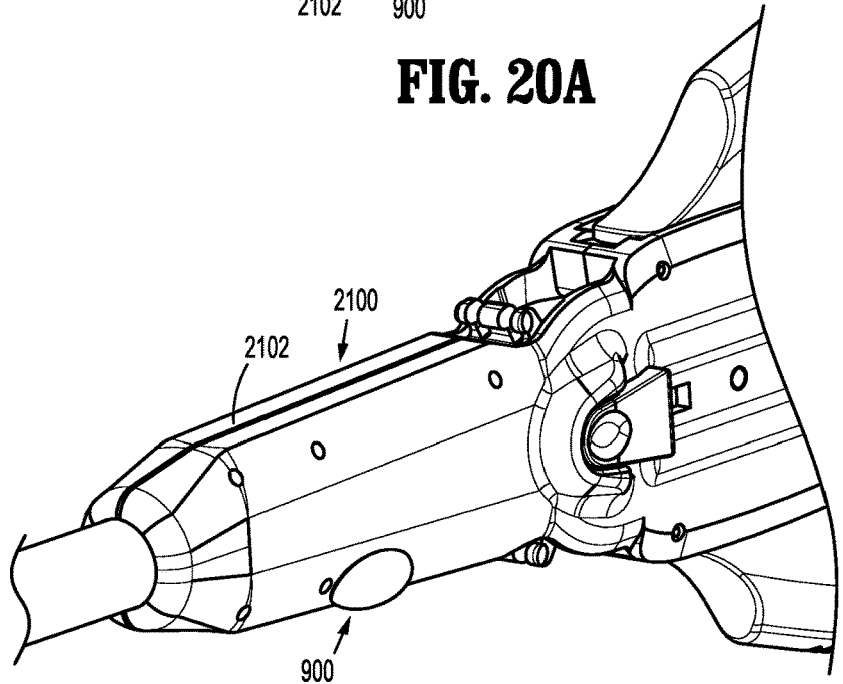
FIGS. 20B and 20C are partial perspective views of the handle assembly of FIG. 20A, illustrating operation of the unloading lock.
Figure 20C:
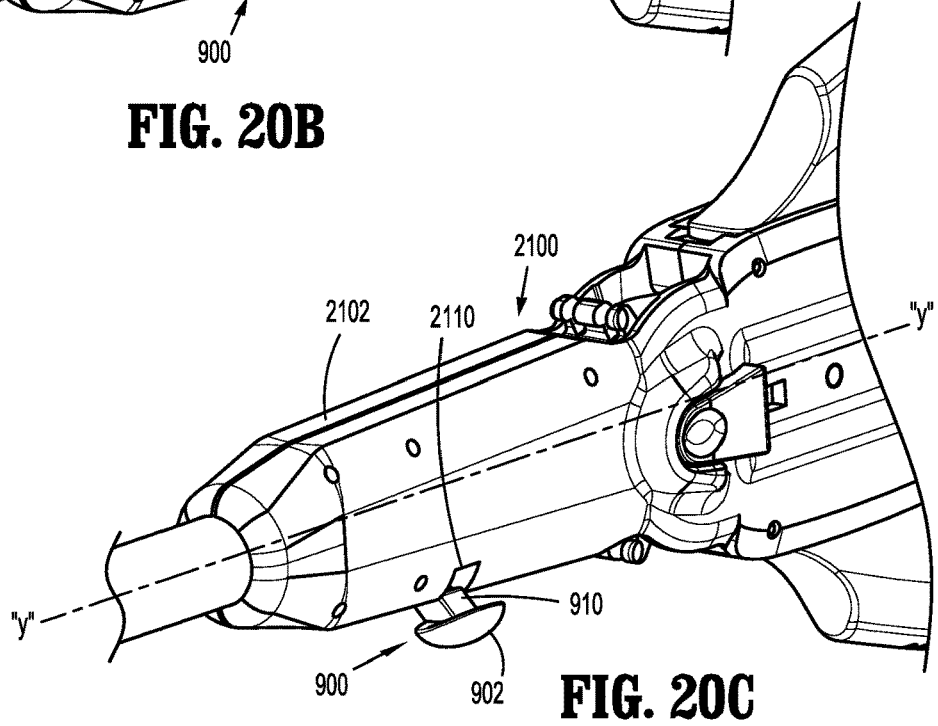

With reference now to FIGS. 20A-20C, there is illustrated a handle assembly 2100 including an unloading lock 900 in accordance with another embodiment of the present disclosure for use with stitching device 1000. Handle assembly 2100 includes features that are identical to the features described with respect to handle assembly 100, and unloading lock 900 includes features that are identical to the features described with respect to unloading lock 600. Thus, the identical parts in handle assembly 2100 and unloading lock 900 will not be described herein to avoid obscuring the present disclosure in unnecessary detail.

As discussed hereinabove with respect to unloading lock 600 (FIGS. 17A-17D), unloading lock 900 is configured to inhibit opening of jaws 130, 132 before needle 104 is released from blades 150, 152 during the unloading process of needle 104. Unloading lock 900 is transitionable between a disengaged position in which pusher 412 (FIG. 6) is movable to a distal-most position, and an engaged position in which unloading lock 900 engages pusher 412 to inhibit distal movement of pusher 412, which, in turn, inhibits opening of jaws 130, 132.

Unloading lock 900 is pivotally secured with housing 2102 to transition unloading lock 900 between the disengaged and engaged positions. Unloading lock 900 includes a head portion 902, a neck portion 910, and an engaging portion (not shown). When unloading lock 900 is in the disengaged position (FIG. 20B), head portion 902 protrudes from housing 2102. Head portion 902 may have an arcuate profile to facilitate operability by the clinician. In addition, as discussed hereinabove with respect to unloading lock 600, the engaging portion (not shown) may define an arcuate recess to enable distal movement of pusher 412 therethrough when loading lock 900 is in the disengaged position.

Housing 2102 defines a notch 2110 dimensioned to, e.g., frictionally, secure neck portion 910 therein. In order to transition unloading lock 900 to the engaged position (FIG. 20C), head portion 902 is pushed transversely outward with respect to a longitudinal axis "Y-Y" defined by handle assembly 2100. When unloading lock 900 is in the engaged position, head portion 902 and neck portion 910 pivot to place the engaging portion in engagement with second cutout 412b of pusher 412 to inhibit distal movement of pusher 412, which, in turn, inhibits opening of jaws 130, 132.

The method of stitching target tissue including unloading of needle 104 from jaws 130, 132 has been described hereinabove and thus will not be described herein to avoid obscuring the present disclosure in unnecessary detail.

Although the illustrative embodiments of the present disclosure have been described herein with reference to the accompanying drawings, the above description, disclosure, and figures should not be construed as limiting, but merely as exemplifications of particular embodiments. For example, the unloading lock may be electro-mechanically actuated to enhance operability of the stitching device. It is to be understood, therefore, that the disclosure is not limited to those precise embodiments, and that various other changes and modifications may be effected therein by one skilled in the art without departing from the scope or spirit of the disclosure.

What is claimed is:

1. An endoscopic stitching device, comprising:
  a handle assembly including:
    a main rod configured for axial displacement;
    a drive conversion assembly including:
      a cam wheel;
      a pivot block;
      first and second links interconnecting the pivot block with the cam wheel;
      a pawl operatively coupled to the main rod, the pawl configured to engage the pivot block to rotate the pivot block which, in turn, causes reciprocating displacement of the first and second links; and
      a pusher secured with the main rod and operatively coupled with the cam wheel; and
    an unloading lock transitionable between an engaged position in which the unloading lock engages the pusher to inhibit distal movement of the pusher, and a disengaged position in which the pusher is disengaged from the unloading lock such that the pusher is movable to a distal-most position; and
  an elongate shaft assembly including:
    first and second blade drive members operatively coupled with the cam wheel; and
    a tool assembly including:
      first and second jaws operatively coupled with the main rod of the handle assembly; and
      first and second blades slidably disposed in the respective first and second jaws, the first and second blades operatively coupled with the first and second blade drive members, respectively, wherein axial displacement of the main rod transitions the first and second jaws between open and closed positions and causes reciprocating axial displacement of the first and second blades.

2. The endoscopic stitching device according to claim 1, wherein the handle assembly includes a housing pivotably supporting the unloading lock.

3. The endoscopic stitching device according to claim 2, wherein the unloading lock includes a first portion and a second portion configured to engage the pusher, the first and second portions defining a curvature such that that when the unloading lock is in the disengaged position, the first portion is flush with the housing and the second portion protrudes from the housing.

4. The endoscopic stitching device according to claim 3, wherein when the unloading lock is in the engaged position the second portion is flush with the housing and the first portion protrudes from the housing.

5. The endoscopic stitching device according to claim 4, wherein the pusher defines a cutout, and the second portion of the unloading lock includes an engaging portion configured to engage the cutout of the pusher.

6. The endoscopic stitching device according to claim 5, wherein the engaging portion of the unloading lock is proximal of the cutout of the pusher when the pusher is in the distal-most position.

7. The endoscopic stitching device according to claim 1, wherein the unloading lock is disposed transverse to a longitudinal axis of the handle assembly.

8. The endoscopic stitching device according to claim 1, wherein the unloading lock is aligned with a longitudinal axis defined by the handle assembly when the unloading lock is in the disengaged position.

9. The endoscopic stitching device according to claim 8, wherein the unloading lock is offset from a longitudinal axis defined by the handle assembly when the unloading lock is in the engaged position.

10. The endoscopic stitching device according to claim 1, wherein the pusher includes walls defining a slot therebetween.

11. The endoscopic stitching device according to claim 10, wherein the unloading lock includes a finger dimensioned to be received in the slot of the pusher to enable axial displacement of the pusher to the distal-most position.

12. The endoscopic stitching device according to claim 11, wherein the finger of the unloading lock is configured to engage the walls to inhibit axial displacement of the pusher to the distal-most position.

13. An endoscopic stitching device, comprising:
a handle assembly including:
a main rod configured for axial displacement;
a tool assembly including:
first and second jaws operatively coupled to the main rod of the handle assembly;
a drive conversion assembly including:
a cam wheel;
a pivot block;
first and second links interconnecting the pivot block with the cam wheel;
a pawl operatively coupled to the main rod, the pawl configured to engage the pivot block to rotate the pivot block which, in turn, causes reciprocating displacement of the first and second links;
third and fourth links operatively coupled with the cam wheel; and
a pusher operatively coupled to the main rod, the pusher engaging the third link to exert force on the cam wheel; and
an unloading lock transitionable between an engaged position in which the unloading lock engages the pusher to inhibit distal movement of the pusher, and a disengaged position in which the pusher is movable to a distal-most position.

14. The endoscopic stitching device according to claim 13, wherein the unloading lock includes a first portion and a second portion including a finger including a width and a length larger than the width.

15. The endoscopic stitching device according to claim 14, wherein the first portion and the finger are rotatable as a single construct.

16. The endoscopic stitching device according to claim 15, wherein the length of the finger is aligned with a longitudinal axis of the handle assembly when the unloading lock is in the engaged position.

17. The endoscopic stitching device according to claim 15, wherein the width of the finger is aligned with a longitudinal axis of the handle assembly when the unloading lock is in the disengaged position.

18. The endoscopic stitching device according to claim 13, wherein the unloading lock includes a first portion and a second portion defining a curvature such that that when the unloading lock is in the disengaged position, the first portion is flush with the housing and the second portion protrudes from the housing.

19. The endoscopic stitching device according to claim 18, wherein when the unloading lock is in the engaged position the second portion is flush with the housing and the first portion protrudes from the housing.

20. The endoscopic stitching device according to claim 18, wherein the second portion includes an engaging portion configured to engage a cutout of the pusher.

21. The endoscopic stitching device according to claim 20, wherein the engaging portion of the second portion is proximal of the cutout of the pusher when the pusher is in the distal-most position.

22. The endoscopic stitching device according to claim 13, wherein the pusher includes walls defining a slot therebetween.

23. The endoscopic stitching device according to claim 22, wherein the unloading lock includes a finger dimensioned to be received in the slot of the pusher to enable axial displacement of the pusher to the distal-most position.

24. The endoscopic stitching device according to claim 13, wherein the unloading lock includes a head portion including an arcuate profile, an engaging portion defining an arcuate recess, and a neck portion connecting the head portion and the engaging portion.

25. The endoscopic stitching device according to claim 24, further comprising a housing, wherein when the unloading lock is in the disengaged position the head portion protrudes from the housing and the arcuate recess of the engaging portion enables passage of the pusher therethrough, and when the unloading lock is in the engaged position, the head portion extends transversely outward from the housing and the engaged portion engages the pusher.

26. The endoscopic stitching device according to claim 25, wherein the housing defines a notch dimensioned to secure the neck portion of the unloading lock when the unloading lock is in the disengaged position.

* * * * *